US010709456B2

(12) United States Patent
Maris et al.

(10) Patent No.: US 10,709,456 B2
(45) Date of Patent: Jul. 14, 2020

(54) COMPRESSION DEVICE AND PRESSURE SENSOR FOR TREATMENT OF ABNORMAL UPPER ESOPHAGEAL SPHINCTER FUNCTIONALITY

(71) Applicants: The Medical College of Wisconsin, Inc., Milwaukee, WI (US); SOMNA THERAPEUTICS, LLC, Germantown, WI (US)

(72) Inventors: Nick T. Maris, Germantown, WI (US); James S. Miller, Germantown, WI (US); Reza Shaker, Brookfield, WI (US); Timothy Bachman, St. Paul, MN (US); Nathan Schlueter, St. Paul, MN (US); Eugene Paul Maloney, St. Paul, MN (US); Eric David North, St. Paul, MN (US); Paul Raine, St. Paul, MN (US); Peter Alex, Germantown, WI (US)

(73) Assignees: The Medical College of Wisconsin, Inc., Milwaukee, WI (US); Somna Therapeutics, LLC, Germantown, WI (US)

( * ) Notice: Subject to any disclaimer, the term of this patent is extended or adjusted under 35 U.S.C. 154(b) by 213 days.

(21) Appl. No.: 15/997,153

(22) Filed: Jun. 4, 2018

(65) Prior Publication Data
US 2018/0280030 A1 Oct. 4, 2018

Related U.S. Application Data

(62) Division of application No. 14/891,117, filed as application No. PCT/US2014/038060 on May 15, 2014, now Pat. No. 10,478,196.
(Continued)

(51) Int. Cl.
A61B 17/132 (2006.01)
A61B 17/135 (2006.01)
(Continued)

(52) U.S. Cl.
CPC ........ A61B 17/135 (2013.01); A61B 17/1325 (2013.01); A61B 17/1327 (2013.01);
(Continued)

(58) Field of Classification Search
CPC . A61B 17/1325; A61B 17/12; A61B 17/1327; A61B 17/135; A61B 2017/00827; A61B 2090/065
See application file for complete search history.

(56) References Cited

U.S. PATENT DOCUMENTS 4,182,344 A 1/1980 Benson
4,243,028 A 1/1981 Puyana
(Continued)

FOREIGN PATENT DOCUMENTS

WO 03099143 A1 12/2003

OTHER PUBLICATIONS

Almond, et al., A 5-Year Prospective Review of Posterior Partial Fundoplication in the Management of Gastroesophageal Reflux Disease, Int. J. Surg., 2010, 8(3):239-242.
(Continued)

Primary Examiner — George J Ulsh
(74) Attorney, Agent, or Firm — Quarles & Brady LLP

(57) ABSTRACT

A compression device is used to increase intra-luminal pressure within the upper esophageal sphincter of a patient in order relieve an impact of an abnormal or defective upper esophageal sphincter anatomy, physiology, or functionality. In one implementation, the compression device is used in conjunction with an external pressure sensing device to determine the external pressure that is to be applied to the
(Continued)

cricoid for a specific patient. The compression device can be a means for the management and/or treatment of abnormal upper esophageal sphincter functionality, or a means for strengthening an esophageal sphincter of a subject, or a means for curing esophageal reflux disease of a subject, or a means for improving vocal function in a subject, or a means for managing lung aspiration, or a means for applying cricoid pressure during anesthesia intubation, or a means for stabilizing body structures such as during medical imaging or radiation treatment.

17 Claims, 14 Drawing Sheets

Related U.S. Application Data

(60) Provisional application No. 61/824,594, filed on May 17, 2013.

(51) Int. Cl.
A61B 17/00 (2006.01)
A61B 90/00 (2016.01)

(52) U.S. Cl.
CPC ............... *A61B 2017/00827* (2013.01); *A61B 2090/065* (2016.02)

(56) References Cited

U.S. PATENT DOCUMENTS

| | | | |
|---|---|---|---|
| 4,354,503 A | 10/1982 | Golden | |
| 4,366,815 A | 1/1983 | Broomes | |
| 4,479,494 A | 10/1984 | McEwen | |
| 4,605,010 A | 8/1986 | McEwen | |
| 4,770,175 A | 9/1988 | McEwen | |
| 4,886,070 A | 12/1989 | Demarest | |
| 4,924,862 A | 5/1990 | Levinson | |
| 4,996,720 A | 3/1991 | Fair | |
| 5,024,240 A | 6/1991 | McConnel | |
| 5,091,992 A | 3/1992 | Pusic | |
| 5,123,425 A | 6/1992 | Shannon, Jr. et al. | |
| 5,181,522 A | 1/1993 | McEwen | |
| 5,366,438 A | 11/1994 | Martin, Sr. | |
| 5,403,266 A | 4/1995 | Bragg et al. | |
| 5,483,974 A | 1/1996 | Crangle | |
| 5,487,383 A | 1/1996 | Levinson | |
| 5,785,670 A | 7/1998 | Hiebert | |
| 5,904,662 A | 5/1999 | Myoga | |
| 6,056,711 A | 5/2000 | Domanski et al. | |
| 6,200,285 B1 | 3/2001 | Towliat | |
| 6,422,873 B1 | 7/2002 | Abdelatti | |
| 8,382,665 B1 | 2/2013 | Fam | |
| 2001/0011543 A1 | 8/2001 | Forsell | |
| 2003/0070684 A1 | 4/2003 | Saied | |
| 2003/0135120 A1 | 7/2003 | Parks et al. | |
| 2004/0097816 A1 | 5/2004 | Just et al. | |
| 2004/0138586 A1 | 7/2004 | Ganz et al. | |
| 2005/0085753 A1 | 4/2005 | Ducharme et al. | |
| 2005/0228302 A1 | 10/2005 | Dalgaard et al. | |
| 2006/0004304 A1 | 1/2006 | Parks | |
| 2006/0194179 A1 | 8/2006 | Abdelatti | |
| 2007/0038132 A1 | 2/2007 | Kishimoto et al. | |
| 2007/0106166 A1 | 5/2007 | Somberg | |
| 2007/0219588 A1 | 9/2007 | Freeman | |
| 2008/0086179 A1 | 4/2008 | Sharma | |
| 2008/0161730 A1 | 7/2008 | McMahon et al. | |
| 2008/0167675 A1 | 7/2008 | Hogosta et al. | |
| 2008/0262479 A1 | 10/2008 | Barela | |
| 2009/0003669 A1 | 1/2009 | Parks et al. | |
| 2009/0044799 A1 | 2/2009 | Qiu | |
| 2009/0300831 A1 | 12/2009 | Welch | |
| 2010/0022987 A1 | 1/2010 | Bochenko et al. | |
| 2011/0202089 A1 | 8/2011 | Sun | |
| 2012/0150215 A1 | 6/2012 | Donald | |
| 2012/0190938 A1 | 7/2012 | Addington et al. | |
| 2013/0090573 A1 | 4/2013 | Shaker | |

OTHER PUBLICATIONS

Aslam, et al., Performance and Optimal Technique for Pharyngeal Impedance Recording: A Simulated Pharyngeal Reflux Study, American Journal of Gastroenterology, 2007, 102:33-39.

Chang, et al., Systematic Review and Meta-Analysis of Randomised Controlled Trials of Gastro-Oesophageal Reflux Interventions for Chronic Cough Associated with Gastro-Oesophageal Reflux, BMJ, doi:10.1136/bmj.38677.559005.55, Published Dec. 5, 2005, 7 pages.

Chen, et al., Sleep Symptoms and Gastroesophageal Reflux, J. Clin. Gastroenterol., 2008, 42:13-17.

DeLegge, Aspiration Pneumonia: Incidence, Mortality, and at-Risk Populations, Journal of Parenteral and Enteral Nutrition, 2002, 26(6):S19-S25.

Dickman, et al., Relationships Between Sleep Quality and pH Monitoring Findings in Persons with Gastroesophageal Reflux Disease, Journal of Clinical Sleep Medicine, 2007, 3(5):505-513.

Dimarino, JR., et al., The Effect of Gastro-Oesophageal Reflux and Omeprazole on Key Sleep Parameters, Alimentary Pharmacology & Therapeutics, 2005, 22:325-329.

Eisenstadt, Dysphagia and Aspiration Pneumonia in Older Adults, Journal of the American Academy of Nurse Practitioners, 2010, 22:17-22.

Ewart, The Efficacy of Cricoid Pressure in Preventing Gastro-Oesophageal Reflux in Rapid Sequence Induction of Anaesthesia, J. Perioper. Pract., 2007, 17(9):432-436.

Farup, et al., The Impact of Nocturnal Symptoms Associated with Gastroesophageal Reflux Disease on Health-Related Quality of Life, Arch. Intern. Med., 2001, 161:45-52.

Fass, et al., Predictors of Heartburn During Sleep in a Large Prospective Cohort Study, Chest, 2005, 127:1658-1666.

Freid, The Rapid Sequence Induction Revisited: Obesity and Sleep Apnea Syndrome, Anesthesiology Clinics of North America, 2005, 23:551-564.

Furnee, et al., Symptomatic and Objective Results of Laparoscopic Nissen Fundoplication After Failed EndoCinch Gastroplication for Gastro-Oesophageal Reflux Disease, European Journal of Gastroenterology & Hepatology, 2010, 22(9)1118-1122.

Gatta, et al., Meta-Analysis: The Efficacy of Proton Pump Inhibitors for Laryngeal Symptoms Attributed to Gastro-Oesophageal Reflux Disease, Alimentary Pharmacology & Therapeutics, 2007, 25:385-392.

Gerson, et al., A Systematic Review of the Definitions, Prevalence, and Response to Treatment of Nocturnal Gastroesophageal Reflux Disease, Clinical Gastroenterology and Hepatology, 2009, 7:372-378.

Hancox, et al., Associations Between Respiratory Symptoms, Lung Function and Gastro-Oesophageal Reflux Symptoms in a Population-Based Birth Cohort, Respiratory Research, 2006, 7:142, 9 pages.

Hunter, et al., A Physiologic Approach to Laparoscopic Fundoplication for Gastroesophageal Reflux Disease, Annals of Surgery, 1996, 223(6):673-687.

King, et al., Trachael Tube Cuffs and Tracheal Dilatation, Chest, 1975, 67:458-462.

Kubota, et al., Tracheal Compression to Prevent Aspiration and Gastric Distension, Can J Anaesth, 1992, 39:2, p. 202.

Kumar, et al., Persistent Pneumonia: Underlying Cause and Outcome, Indian Journal of Pediatrics, 2009, 76 (12):1223-1226.

Landsman, Cricoid Pressure: Indications and Complications, Pediatric Anesthesia, 2004, 14(1):43-47.

Lawes, et al., The Cricoid Yoke—A Device for Providing Consistent and Reproducible Cricoid Pressure, British Journal of Anaesthesia, 1986, 58(8):925-931.

Locke, et al., Prevalence and Clinical Spectrum of Gastroesophageal Reflux: A Population-Based Study in Olmsted county, Minnesota, Gastroenterology, 1997, 112:1448-1456.

(56) References Cited

OTHER PUBLICATIONS

McGuigan, et al., Review Article: Diagnosis and Management of Night-Time Reflux, Alimentary Pharmacology & Therapeutics, 2004, 20(Suppl. 9):57-72.
Mylotte, et al., Pneumonia Versus Aspiration Pneumonitis in Nursing Home Residents: Prospective Application of a Clinical Algorithm, J. Am. Geriatr. Soc., 2005, 53:755-761.
Neilipovitz, et al., No Evidence for Decreased Incidence of Aspiration After Rapid Sequence Induction, Can. J. Anesth., 2007, 54:9, pp. 748-764.
Orr, Review Article: Sleep-Related Gastro-Oesophageal Reflux as a Distinct Clinical Entity, Alimentary Pharmacology & Therapeutics, 2010, 31:47-56.
Palombini, et al., A Pathogenic Triad in Chronic Cough—Asthma, Postnasal Drip Syndrome, and Gastroesophageal Reflux Disease, Chest, 1999, 116:279-284.
Parry, Teaching Anaesthetic Nurses Optimal Force for Effective Cricoid Pressure: A Literature Review, Nursing in Critical Care, 2009, 14(3):139-144.
Pfitzner, et al., Controlled Neck Compression in Neurosurgery, Anaesthesia, 1985, 40(7):624-629.
Priebe, Cricoid Pressure: An Experts Opinion, Minerva Anestesiologica, 2009, 75(12):710-714.
Rakita, et al., Laparoscopic Nissen Fundoplication Offers High Patient Satisfaction with Relief of Extraesophageal Symptoms of Gastroesophageal Reflux Disease, The American Surgeon, 2006, 72:207-212.
Roka, et al., Prevalence of Respiratory Symptoms and Diseases Associated with Gastroesophageal Reflux Disease, Digestion, 2005, 71:92-96.
Sale, Prevention of Air Embolism During Sitting Neurosurgery, Anaesthesia, 1984, 39(8):795-799.
Shaker, et al., Nighttime Heartburn Is an Under-Appreciated Clinical Problem That Impacts Sleep and Daytime Function: The Results of a Gallup Survey Conducted on Behalf of the American Gastroenterological Association, The American Journal of Gastroenterology, 2003, 98(7):1487-1493.
Shaker, et al., Intrapharyngeal Distribution of Gastric Acid Refluxate, The Laryngoscope, 2003, 113:1182-1191.
Shaker, Nighttime Gerd: Clinical Implications and Therapeutic Challenges, Best Practice & Research Clinical Gastroenterology, 2004, 18(S):31-38.
So, et al., Outcomes of Atypical Symptoms Attributed to Gastroesophageal Reflux Treated by Laparoscopic Fundoplication, Surgery, 1998, 124:28-32.
Stroud, et al., Management of Intractable Aspiration, Oct. 18, 2000, 10 pages.
Suiter, et al., Effects of Cuff Deflation and One-Way Tracheostomy Speaking Valve Placement on Swallow Physiology, Dysphagia, 2003, 18:284-292.
Ulualp, et al., Pharyngo-UES Contractile Reflex in Patients with Posterior Laryngitis, The Laryngoscope, 1998, 108 (9):1354-1357.
Vanner, et al., Upper Oesophageal Sphincter Pressure and the Effect of Cricoid Pressure, Anaesthesia, 1992, 47:95-100.
Wileman, et al., Medical Versus Surgical Management for Gastro-Oesophageal Reflux Disease (GORD) in Adults (Review), The Cochrane Library, 2010, Issue 4, 39 pages.
Young, et al., Evaluation of a New Design of Tracheal Tube Cuff to Prevent Leakage of Fluid to the Lungs, British Journal of Anaesthesia, 1998, 80:796-799.
PCT International Search Report, PCT/US2011/035050, dated Oct. 25, 2011, 2 pages.
PCT International Preliminary Report on Patentability, PCT/US2011/035050, dated Dec. 4, 2012, 23 pages.
PCT International Search Report and Written Opinion, PCT/US2014/38060, dated Nov. 21, 2014, 27 pages.

COMPRESSION DEVICE AND PRESSURE SENSOR FOR TREATMENT OF ABNORMAL UPPER ESOPHAGEAL SPHINCTER FUNCTIONALITY

CROSS-REFERENCES TO RELATED APPLICATIONS

This application is a divisional application of U.S. patent application Ser. No. 14/891,117 filed Nov. 13, 2015, which is a 371 application of PCT/US2014/038060 filed May 15, 2014, which claims priority from U.S. Provisional Patent Application No. 61/824,594 filed May 17, 2013.

STATEMENT REGARDING FEDERALLY SPONSORED RESEARCH

Not Applicable.

BACKGROUND OF THE INVENTION

1. Field of the Invention

This invention relates to the detection, prevention, treatment and cure of gastroesophageal and gastroesophagopharyngeal reflux complications. It also relates to methods for improving vocal function, methods for managing lung aspiration, methods for applying cricoid pressure during anesthesia intubation, and methods for stabilizing body structures such as during medical imaging or radiation treatment.

2. Description of the Related Art

Aspiration of gastric contents into the lung and airway as well as regurgitation of stomach contents into pharynx and larynx is the reason for a significant number of office visits and hospitalizations. Although morbidity of this condition is not systematically evaluated, a significant percent of deaths has been attributed to the aspiration of gastric content (30-70% of patients with aspiration pneumonia). In addition, a substantial number of outpatient visits are prompted by entry of gastric contents into structures above and beyond the esophagus resulting in various complaints and disorders. These include pneumonia, pneumonitis, bronchitis, laryngitis, pharyngitis, otitis media, laryngeal cancer, dental erosion, and asthma, for example. These conditions cause symptoms such as chronic cough (reflux is the cause in 29% in some studies), frequent throat clearing, sensation of a lump in the throat (globus), excessive phlegm, hoarse voice, ear ache, fever, and productive cough in case of pneumonia.

The most deleterious regurgitation events and aspirations occur in recumbent positions and during sleep. For example, nocturnal acid reflux sufferers often grapple with esophagitis and stricture, adenocarcinnoma of the esophagus, respiratory, and ear, nose and throat disorders, as well as sleep disturbances and diminished quality of life. These complications during sleep further exacerbate the day-time symptoms of chronic cough, frequent throat clearing, or other symptoms.

Acid suppressive therapy has been used as a treatment strategy for gastroesophageal and gastroesophagopharyngeal reflux. However, studies of effective acid suppression using proton pump inhibitors, H2 receptor antagonists have, at best, reported a modest improvement which has been challenged by properly designed randomized clinical trials. In some instances, pharmacologic therapy has been combined with elevation of the head of the bed or avoidance of eating for three to four hours before retiring to sleep but these methods have not given rise to significant improvements.

Surgical studies of the management of these therapies report success in some patients. These surgical procedures, however, are costly and have some mortality, but significant morbidity including difficulty swallowing, gas bloat syndrome, diarrhea, weight loss, . . . etc. These complications frequently necessitate redo or revision of the operation. In addition, these procedures do not last permanently and lose their efficacy within seven to ten years.

The socio-economic impact of the available medical and surgical therapy for the reflux induced supra esophageal complications and aspirations described above is significant and adds many billions to the health care burden.

U.S. Patent Application Publication No. 2013/0090573 describes a device and method that overcome the limitations of the gastroesophageal and gastroesophagopharyngeal reflux treatment therapies described above. Specifically, U.S. 2013/0090573 discloses a non-pharmacologic device that is used to increase intra-luminal pressure within the upper esophageal sphincter (UES) of a patient, such as a human or animal, in order to prevent entry of gastric contents into the pharynx, larynx, or a lung. The device uses external pressure to induce intra-luminal pressure within the UES, by compressing the UES between a cricoid cartilage and a cervical vertebrae thereby preventing gastroesophageal and gastroesophagopharyngeal reflux. The induced intra-luminal pressure, however, does not occlude the esophagus under all physiological events.

In view of the advances in gastroesophageal and gastroesophagopharyngeal reflux therapy provided by U.S. 2013/0090573, further improvements to this gastroesophageal and gastroesophagopharyngeal reflux treatment technology are desirable.

SUMMARY OF THE INVENTION

The present invention provides a compression device for reducing pharyngeal reflux in a subject. The compression device includes a frame; a strap having a first end section attached to the frame and an opposite second end section attached to the frame, wherein a length of the strap between the first end section and the second end section is adjustable; and a cushion disposed on the frame. The strap and frame are configured to position the cushion over a cricoid of the subject and to apply a predetermined amount of pressure to the cricoid in order to reduce pharyngeal reflux in the subject while allowing the subject to open an upper esophageal sphincter of the subject for other physiological events.

The compression device may include an adjustment mechanism for moving the cushion toward or away from the frame. The adjustment mechanism can vary the curvature of the frame when moving the cushion toward or away from the frame. The adjustment mechanism can be centrally located on the frame. The adjustment mechanism may include a plate and a position adjustor movably attached to the plate. The position adjustor is located on a first side of the frame, and the plate has a first surface and an opposite second surface. The first surface of the plate can be attached to the cushion, the second surface of the plate can be in contact with a second side of the frame. The second surface of the plate can include spaced apart outwardly extending walls that contact with the second side of the frame. The cushion may be removably attached to the first surface of the plate using a fastener material.

In one version of the compression device, the position adjustor is rotatable with respect to the plate such that rotation of the position adjustor in a first direction moves the cushion toward the frame and rotation of the position adjustor in a second direction moves the cushion away from the frame. One of the position adjustor and the plate can include an internally threaded hole, and the other of the position adjustor and the plate can include an externally threaded post, wherein the internally threaded hole engages the externally threaded post for translation of the position adjustor relative to the plate.

In one version of the compression device, the first end section of the strap is looped through a slot of the frame for attaching the first end section of the strap to the frame. An amount of the strap looped through the slot of the frame can be varied to adjust the length of the strap between the first end section and the second end section of the strap. The amount of the strap looped through the slot of the frame can be varied by using a fastener material that can removably engage the strap. The second end section of the strap can be attached to a clasp for securing the second end section of the strap to the frame. The second end section of the strap can be looped through a slot of the clasp for attaching the second end section of the strap to the clasp. The first end section of the strap and the second end section of the strap may be removably attached to the frame.

The present invention also provides a pressure sensing device that can be used with the compression device for determining a configuration of the compression device suitable for an individual patient. The pressure sensing device includes a pouch defining an interior space containing a spacing insert and a fluid; a conduit having a first end in fluid communication with the interior space of the pouch; and a pressure sensor in fluid communication with a second end of the conduit wherein the pressure sensor and the pouch and the conduit define a fluid tight closed volume. The pressure sensor may include a sensing layer and a sensing element in contact with the sensing layer wherein the sensing element generates a pressure signal when the fluid applies pressure to the sensing layer. The pressure sensing device also includes a display device; and a controller in electrical communication with the pressure sensor and the display device. The controller executing a stored program to: (i) receive the pressure signal from the pressure sensor; (ii) correlate the pressure signal to an applied pressure on the pouch; and (iii) display the applied pressure on the display device.

In one version of the pressure sensing device, the sensing layer comprises a silicon diaphragm. The sensing layer may have a first side and an opposite second side, wherein the first side senses a pressure of the fluid and the second side senses ambient atmospheric pressure. The sensing element can be a strain gauge such that the pressure signal is an output voltage.

In one version of the pressure sensing device, the pouch comprises two pieces of polymeric film having a thickness in the range of 0.001 to 0.020 inches, the pouch has a surface area of about 1 to about 10 square inches, and the interior space of the pouch has a volume of about 0.01 cubic inches to about 1 cubic inch. The pouch and the conduit can be heat sealed together, may be disposable, and can be provided in packaging. The insert can have a perimeter similar in shape to a perimeter of the pouch.

The pressure sensing device may include a housing, wherein the housing contains the pressure sensor and the controller, and the housing supports the display device. The conduit can be removably connected to the housing using a Luer taper connection.

In the pressure sensing device, the fluid is used to take the pressure measurement. The pouch, conduit and pressure sensor are singular in that there is one sealed pouch, conduit and pressure sensor. The sealed pouch is unsupported and floats between two surfaces. The sealed pouch surfaces are soft, and sealed pouch deformation is not part of the pressure measurement. The pressure sensing device is mobile, small, lightweight, self-contained with one hand operation, and automatic operation after the on button is pushed.

The present invention also provides an esophageal sphincter compression kit comprising a compression device including a cushion; and a pressure sensing device configured to measure pressure between the cushion and a neck of a subject when the pressure sensing device is positioned between the cushion and the neck of the subject. The compression device may be a compression device according to the present disclosure. The pressure sensing device may be a pressure sensing device according to the present disclosure. The sealed pouch of the pressure sensing device is placed in an exact anatomical position (e.g., on the cricoid cartilage) when using the kit. The sealed pouch of the pressure sensing device bag is of a predetermined volume, specific to the desired application (e.g., reducing pharyngeal reflux in a subject) of the compression device.

The present invention also provides a method for reducing reflux above an upper esophageal sphincter of a subject by increasing an intra-luminal pressure of the upper esophageal sphincter of the subject. In the method, a pressure sensing device is positioned on the neck of the subject over a cricoid of the subject. A compression device is used to apply an external pressure to the pressure sensing device until the pressure sensor denotes that the pressure is within a predetermined range. The denoted pressure is associated with a value of an indicator of the compression device. The pressure sensing device and compression device are removed from the subject; and the compression device is reapplied around the neck of the subject according to the value such that the cushion applies pressure to the cricoid of the subject. The value may indicate alignment of two reference lines on an adjustable strap of the compression device. The predetermined range of pressure can be 10-70 mm Hg, preferably 20-30 mm Hg. The predetermined range of pressure correlates to an amount of pressure to the cricoid that reduces pharyngeal reflux in the subject while allowing the subject to open the upper esophageal sphincter for other physiological events. The predetermined range of pressure may correlate about 1:1 to the amount of pressure to the cricoid that reduces pharyngeal reflux in the subject while allowing the subject to open the upper esophageal sphincter for other physiological events. In the method, the compression device may be a compression device according to the present disclosure, and the pressure sensing device may be a pressure sensing device according to the present disclosure.

The present invention also provides a method for strengthening an esophageal sphincter of a subject. The method uses a compression device including (i) a frame, (ii) a strap having a first end section attached to the frame and an opposite second end section attached to the frame, and (iii) a cushion disposed on the frame. The compression device is positioned around a neck of the subject such that the cushion applies pressure on the neck that is transmitted to the esophageal sphincter of the subject. For a plurality of times, the compression device is removed from the subject, and the compression device is reapplied around the neck of the subject such that the cushion applies pressure on the neck that is transmitted to the esophageal sphincter of the subject. As result of this periodic use of the compression device, the esophageal sphincter of the subject is strengthened. The compression device may be positioned around the neck of the subject while the subject is sleeping. In the method, the compression device may be a compression device according to the present disclosure. Although the compression device will most often be worn at night, certain physicians may believe that a subject will need and will wear the compression device during the day. Certain doctors may say up to 40% of subjects will wear the compression device during the day. Thus, while the compression device is primarily a night time device, the compression device can/will also be utilized/worn during the day.

In the method for strengthening an esophageal sphincter of a subject, the method also include the step of placing an electrode in contact with the neck of the subject, placing an electrical pulse generator in electrical communication with the electrode, activating the electrical pulse generator to generate a series of electrical pulses from the electrode such that the series of electrical pulses electrically stimulate the esophageal sphincter of the subject. The electrode may be attached to the cushion.

In the method for strengthening an esophageal sphincter of a subject, the method may also include the step of placing one or more electrodes adjacent the esophageal sphincter, placing an electrical pulse generator in electrical communication with each electrode, activating the electrical pulse generator to generate a series of electrical pulses from the electrode(s) such that the series of electrical pulses electrically stimulate the esophageal sphincter of the subject.

In the method for strengthening an esophageal sphincter of a subject, the method may also include the step of placing one or more electrodes in the esophageal sphincter, placing an electrical pulse generator in electrical communication with the electrode(s), activating the electrical pulse generator to generate a series of electrical pulses from the electrode(s) such that the series of electrical pulses electrically stimulate the esophageal sphincter of the subject.

The present invention also provides a method for strengthening an upper esophageal sphincter of a subject. The method includes the steps of placing one or more electrodes near the upper esophageal sphincter of the subject; placing an electrical pulse generator in electrical communication with each electrode; and activating the electrical pulse generator to generate a series of electrical pulses from the electrode(s) such that the series of electrical pulses electrically stimulate the upper esophageal sphincter of the subject. In the method, the electrode(s) can be placed in contact with a neck of the subject. In the method, the electrode(s) can be placed on an esophagus of the subject. In the method, the electrode(s) can be placed in the upper esophageal sphincter of the subject.

The present invention also provides a method for curing esophageal reflux disease of a subject. The method uses a compression device including (i) a frame, (ii) a strap having a first end section attached to the frame and an opposite second end section attached to the frame, and (iii) a cushion disposed on the frame. The compression device is positioned around a neck of the subject such that the cushion applies pressure to a cricoid of the subject. For a plurality of times, the compression device is removed from the subject, and the compression device is reapplied around the neck of the subject such that the cushion applies pressure on the cricoid of the subject. As result of this periodic use of the compression device, esophageal reflux disease of the subject is cured. The compression device may be positioned around the neck of the subject while the subject is sleeping. In the method, the compression device may be a compression device according to the present disclosure.

The present invention also provides a method for improving vocal function in a subject. In the method, a cushion of a compression device is positioned over a voice box region of a neck of the subject such that the compression device applies pressure to the voice box region of the neck of the subject. In the method, the compression device may be a compression device according to the present disclosure These and other features, aspects, and advantages of the present invention will become better understood upon consideration of the following detailed description, drawings and appended claims.

BRIEF DESCRIPTION OF THE DRAWINGS

FIG. 3b is a side view of the device of FIG. 3a;

Like reference numerals will be used to refer to like parts from Figure to Figure in the following description of the drawings.

DETAILED DESCRIPTION OF THE INVENTION

A non-pharmacologic device is used to increase intra-luminal pressure within the upper esophageal sphincter (UES) of a patient, such as a human or animal, in order to prevent entry of gastric contents into the pharynx, larynx, or a lung. The device uses external pressure to induce intra-luminal pressure within the UES, by compressing the UES between a cricoid cartilage and a cervical vertebrae and preventing gastroesophageal and gastroesophagopharyngeal reflux. The induced intra-luminal pressure, however, does not occlude the esophagus under all physiological events. The compression device is used to maintain the intra-luminal pressure of the patient within a predetermined range, continuously reinstating the competency of the UES over a period of time. In certain implementations, the intra-luminal UES pressure is induced by applying an external pressure to a patient's cricoid transferring a compressive force through the intermediary tissue of the patient towards the UES, increasing its intra-luminal pressure.

In certain implementations, the intra-luminal UES pressure is kept within the predetermined range while the patient is asleep. Normal resting pressure of the UES is about 40 mm Hg in the elderly and about 70 mm Hg in the young. The driving pressure of the majority of reflux events are less than 20 mm Hg. During sleep, the intra-luminal UES pressure may decline to approximately 10 mm Hg, potentially rendering the UES incompetent to maintain the barrier against aspiration. Here, the compression device may be used to induce the intra-luminal pressure to remain within a range that is about 10-70 mm Hg, such as about 20-40 mm Hg during sleep, for example. Therefore, the induced intra-luminal pressure effectively prevents gastroesophageal reflux from entering the pharynx and subsequently in the larynx and the lung during sleep. The terms "UES pressure," "intra-luminal pressure," and "intra-luminal UES pressure" are used interchangeably herein.

Figure 1:
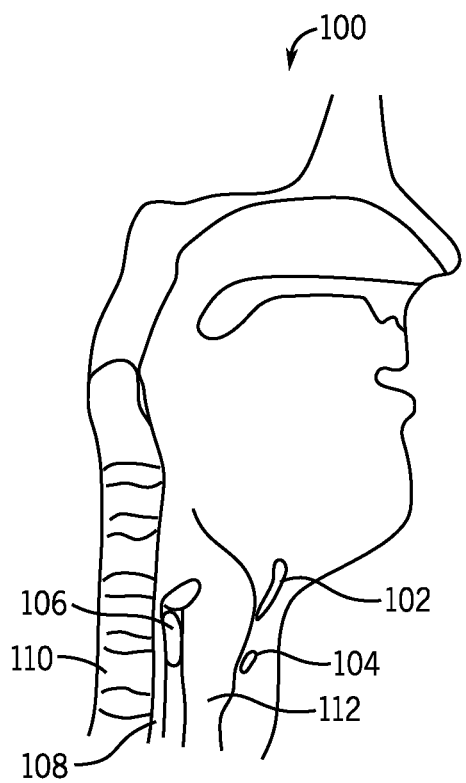
FIG. 1 is a schematic diagram depicting a sagittal cross section of a nose, mouth, pharynx, and larynx of a patient.

Referring to FIG. 1, a schematic diagram depicting a sagittal cross section 100 of a nose, mouth, pharynx, larynx, and esophagus of a patient. The cricoid cartilage is a semi-circular cartilage just above the trachea 112. The posterior portion of the cricoid 106 is located just anterior to the UES of the esophagus 108 and is typically broader than the anterior portion of the cricoid 104 that sits just inferior to the thyroid cartilage 102 (Adam's apple) in the neck. The crico-pharyngeous muscle, the main component of the UES (not shown) is a "C" clamp-shaped muscle that attaches to the posterior lamina of the cricoid just distal to the thyroid cartilage 102. Behind the crico-pharyngeous muscle is the cervical vertebrae 110. Therefore, crico-pharyngeous muscle, the main component of the UES and chief barrier against reflux and aspiration into the airway, is located between the vertebrae and the cricoid cartilage giving rise to the opportunity for increasing the UES intra-luminal pressure by external application of pressure onto the cricoid cartilage.

In one implementation, a non-invasive UES compression device is used in conjunction with an external pressure sensing device (collectively "kit") to determine the external pressure that is to be used within a predetermined range for a specific patient. The non-invasive UES compression device can be used to apply an external pressure that changes the intra-luminal pressure of the patient within the predetermined range.

Figure 2:
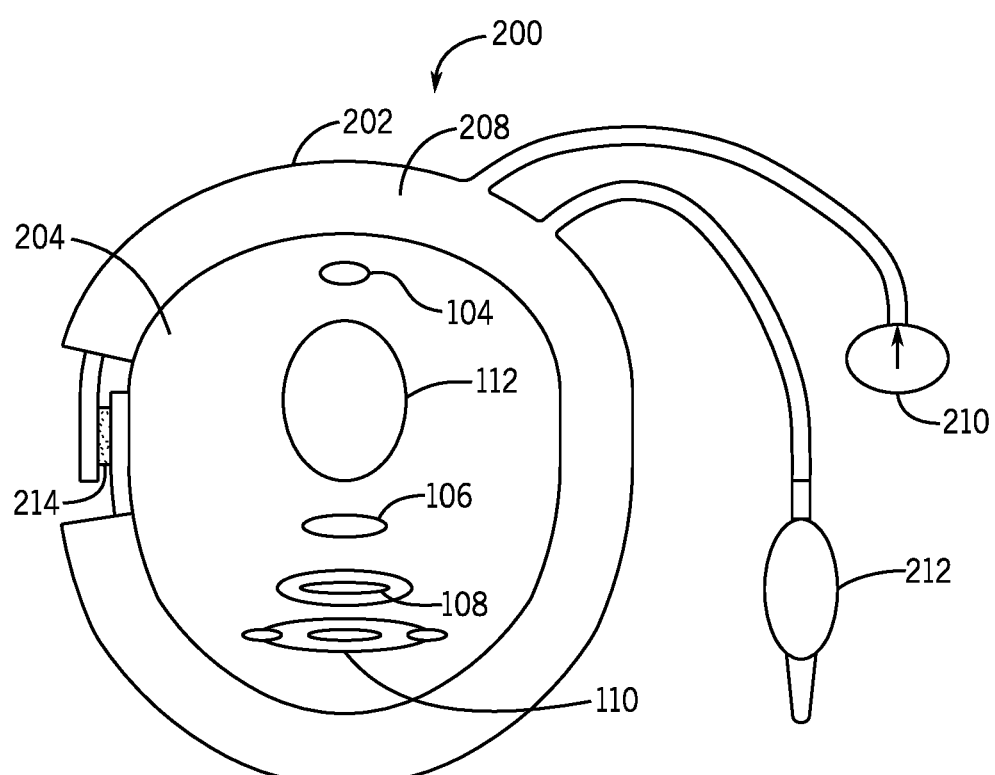
FIG. 2 is a schematic diagram depicting a transverse cross section of a patient's neck encircled by one example implementation of a device that compresses the UES of the patient.

Referring to FIG. 2, a schematic diagram depicts a transverse cross section 200 of an example UES compression device 202 applied to a patient's neck 204. The UES compression device 202 in FIG. 2 is illustrated as having an inflatable cuff 208, a gauge 210, and a bulb 212 for manual insertion of pressurized air into the inflatable cuff 208. The inflatable cuff 208 can be inflated by squeezing the bulb 212.

The pressure produced by the cuff 208 can then be read using the gauge 210. The gauge 210 may be connected to the cuff 208 via a tube that is long enough for the patient to be able to read the gauge 210. In other implementations, the bulb 212 may be replaced with means to automatically insert pressurized air into the inflatable cuff 208, such as an air pump. The inflatable cuff 208 may have a coupling means 214 to couple the two ends of the inflatable cuff together when wrapped around the neck of the patient. Examples of the coupling means 214 include a hook-and-loop fastener, a fastener with female and corresponding male connectors, or mechanical securement devices, for example.

Figure 3A:
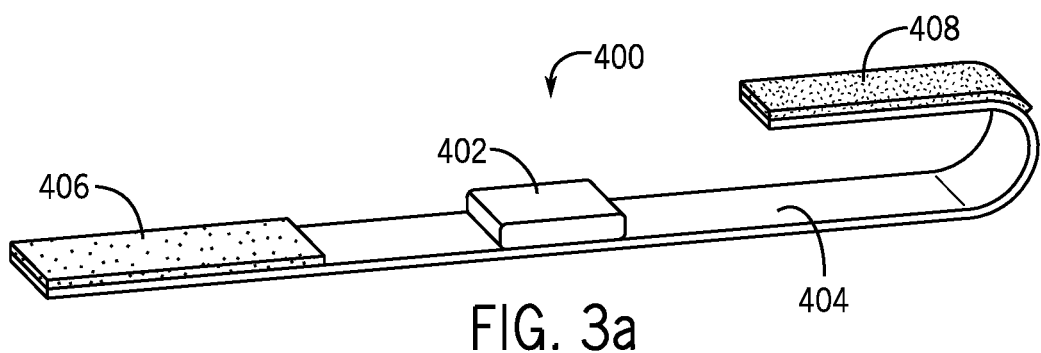
FIG. 3a is a perspective view of yet another example implementation of a device that compresses the UES of the patient.
Figure 3B:
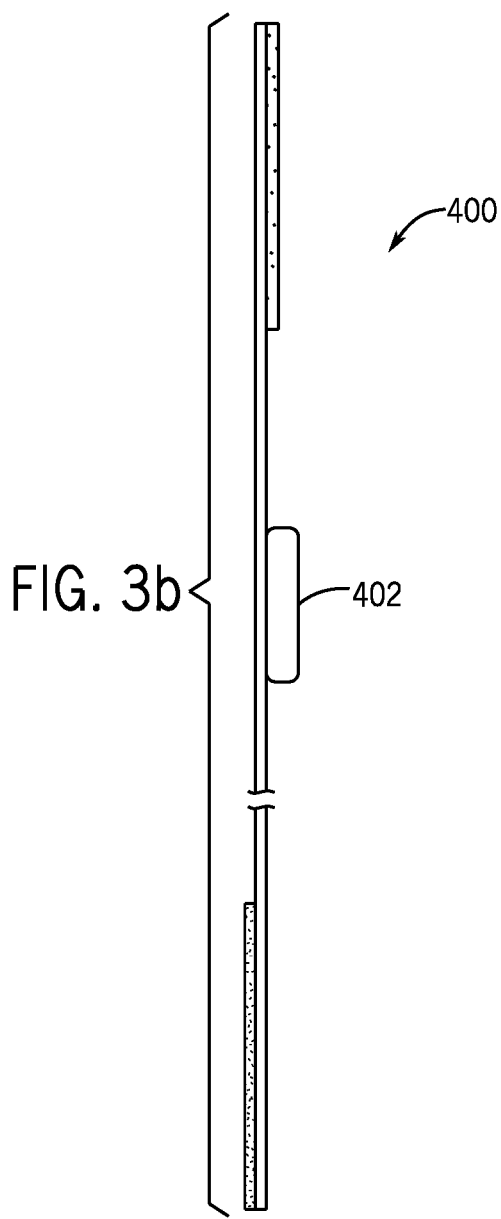

Referring to FIGS. 3a and 3b, another example of the UES compression device 400 is depicted. The UES compression device 400 includes a cushion 402 and a band 404. Here, the UES compression device 400 employs a hook-and-loop means (e.g., a Velcro® fastener) to couple the first end 406 and second end 408 of the band 404 together. The first end 406 is shown in FIG. 3a as the loop end and the second end 408 is shown as the hook end of the hook-and-loop fastener. Once coupled, the length along the long axis of the band 404, of the UES compression device 400 is directly related to the intra-luminal pressure. Alternatively, or in combination, the length is varied to obtain the desired intra-luminal pressure by applying less external pressure. In certain implementations, the length of the cushion 402 along the long axis of the cushion 402 and a thickness of the cushion 402 is configured to apply minimal external pressure to the vascular structures within the neck, such as the carotid artery or the jugular veins. For example, the thickness of the cushion 402 allows for a gap of air between the compression device 400 and the neck in the proximity of the vascular structures. Here, the band 404 bridges over the carotid and jugular vein avoiding compression of these vital organs. The aforementioned bridge is between the cushion and sternocleidomastoid muscle.

The implementations disclosed are non-limiting. Other implementations are also contemplated. For example, the implementation in FIGS. 3a and 3b may have a different type of coupling means that resembles the clasp of a belt buckle, or the material of the UES compression device 400 may be elastic. Moreover, the features of the various implementations may be mixed and matched such as utilizing the tightening means in one implementation in another implementation.

Figure 4:
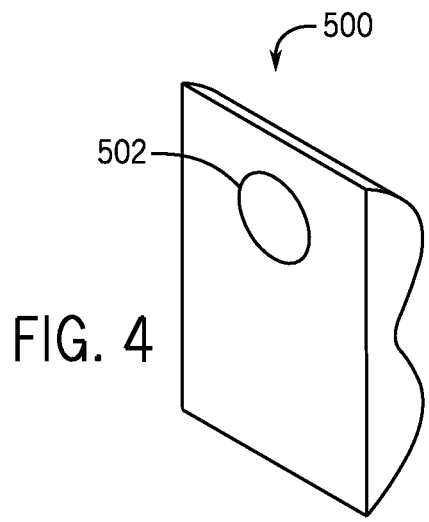
FIG. 4 is a perspective view of an another example cushion used to compress the UES of the patient.
Figure 5:
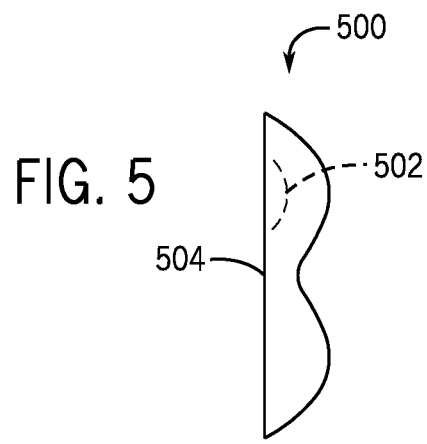
FIG. 5 is a side view of the cushion of FIG. 4.

FIGS. 4 and 5 illustrate an implementation of the cushion 500 that might be employed with the UES compression devices 200 or 400. FIG. 4 is a perspective view and FIG. 5 is a side view of the cushion 500. The cushion 500 has a recession 502 that dimples the medial 504 portion of the cushion 500. When the cushion 500 is placed over the anterior portion of the patient's neck, the recession 502 is positioned over the tracheal cartilage ("Adam's Apple") of the patient's neck and the area just beneath the recession 502 is positioned over the cricoid. In this manner, recession 502 can act as an anchor, preventing displacement of the cushion during sleep. This can assist in maintaining the pressure against the cricoid within the predetermined range.

Turning now to FIGS. 6 to 9, yet another example of a compression device 600 is shown. The compression device 600 has a frame 610 that can comprise a polymeric material such as polyethylene, polypropylene, nylon, polyester, acrylonitrile butadiene styrene, and the like. The frame 610 has a central section 612 with a central aperture 613. A first section 616 of the frame 610 extends laterally from the central section 612. The first section 616 has a outer end 618 with a vertical slot 619, and the first section 616 has an inner end 621 with an arcuate recess 622. On the side of the first section 616 opposite the recess 622, there are mounting slots 623. A second section 626 of the frame 610 extends laterally from the central section 612. The second section 626 has an outer end 628 with a vertical slot 629, and the second section 626 has an inner end 631 with an arcuate recess 632. On the side of the second section 626 opposite the recess 632, there are mounting slots 633.

Still referring to FIGS. 6 to 9, the compression device 600 has an adjustment plate 652 having an externally threaded post 654 with a central internally threaded hole 655. The adjustment plate 652 has a first wall 658 with a protrusion 659, and a laterally spaced apart second wall 661 with a protrusion 662. The compression device 600 also has a spacer 664 with an opening 665, and has a dial 667 with an internally threaded throughhole 668. The compression device 600 has a screw 670 and a washer 671, and an adjustment knob 673.

The adjustment plate 652, the spacer 664, the dial 667, the screw 670, the washer 671, and the adjustment knob 673 can be assembled into a curvature adjustment mechanism for the frame 610 as follows. On one side of the frame 610, the protrusion 659 and the protrusion 662 of the adjustment plate 652 are positioned in one of the mounting slots 623 and one of the mounting slots 633, respectively. The spacer 664 is positioned in contact with the central section 612 of the frame 610 on the opposite side of the frame 610. The dial 667 is positioned in contact with the spacer 664 between the arcuate recess 622 and the arcuate recess 632 of the frame 610. The screw 670 is assembled in the washer 671, and the screw 670 is passed through the throughhole 668 of the dial 667, through the opening 665 of the spacer 664, through the aperture 613 of the frame 610, and into the threaded hole 655 of the adjustment plate 652. The adjustment knob 673 can be snapped on the dial 667.

The adjustment mechanism for the frame 610 functions as follows. The central section 612 of the frame 610 has a reduced front to rear thickness compared to the front to rear thickness of the first section 616 and the second section 626 of the frame 610. As a result, the first section 616 and the second section 626 of the frame 610 can flex with respect to the central section 612 of the frame 610 in directions A and B as shown in FIG. 8. When the adjustment knob 673 is rotated in one of the directions R in FIG. 7, movement of the externally threaded post 654 of the adjustment plate 652 in the internally threaded throughhole 668 of the dial 667 due to engagement of the threads of the post 654 and the throughhole 668 causes the adjustment plate 652 and the dial 667 to move together. When the adjustment knob 673 is rotated in the opposite direction of directions R in FIG. 7, movement of the externally threaded post 654 of the adjustment plate 652 in the internally threaded throughhole 668 of the dial 667 causes the adjustment plate 652 and the dial 667 to move apart.

As detailed above, the protrusion 659 and the protrusion 662 of the adjustment plate 652 are positioned in one of the mounting slots 623 and one of the mounting slots 633 of the first section 616. This causes contact of the first wall 658 of the adjustment plate 652 with the first section 616 of the frame 610, and causes contact of the second wall 661 of the adjustment plate 652 with the second section 626 of the frame 610. When the adjustment plate 652 and the dial 667 move together, the first wall 658 of the adjustment plate 652 moves the first section 616 of the frame 610 in direction A of FIG. 8 with respect to the central section 612 of the frame 610, and the second wall 661 of the adjustment plate 652 moves with the second section 626 of the frame 610 in direction A of FIG. 8 with respect to the central section 612 of the frame 610. Due to the elastic property of the central section 612 of the frame 610, when the adjustment plate 652 and the dial 667 move apart, the first section 616 of the frame 610 moves in direction B of FIG. 8 with respect to the central section 612 of the frame 610, and the second section 626 of the frame 610 moves in direction B of FIG. 8 with respect to the central section 612 of the frame 610. The choice of left handed or right handed threads for the externally threaded post 654 of the adjustment plate 652 and the internally threaded throughhole 668 of the dial 667 determines whether rotation of the adjustment knob 673 in the clockwise direction of directions R in FIG. 7 causes movement in direction A or direction B for the first section 616 and the second section 626 of the frame 610.

The compression device 600 has a fastener material 678, such as the hook or loop fastening material of a Velcro® fastener. The compression device 600 has a cushion 680 that may be fastened to the adjustment plate 652 by the fastener material 678. The hook and loop portions of the fastening material 678 can each be secured to the adjustment plate 652 and the cushion 680 by adhesive or other suitable means.

Figure 6:
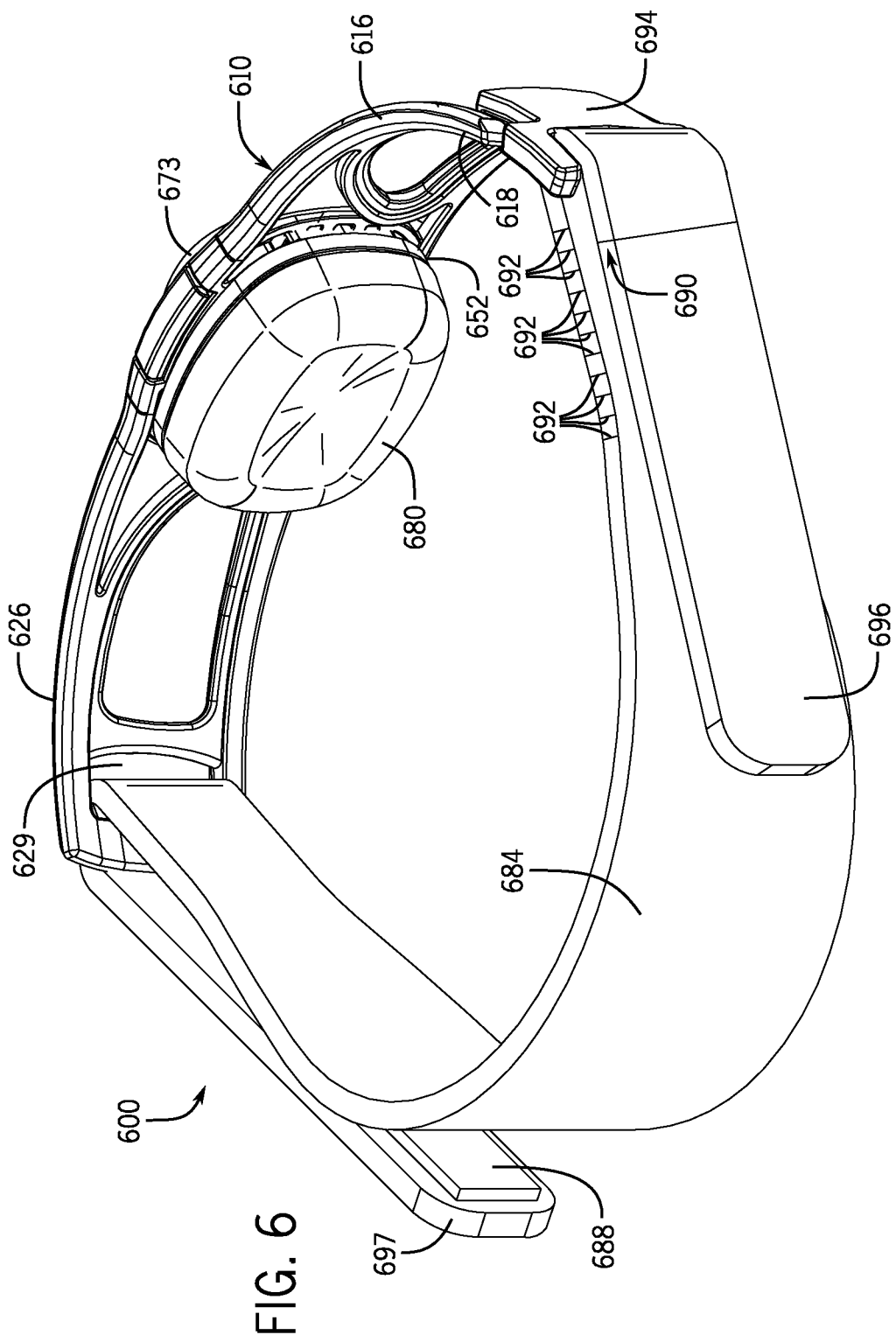
FIG. 6 is a right rear perspective view of yet another example implementation of a device that compresses the UES of the patient.
Figure 7:
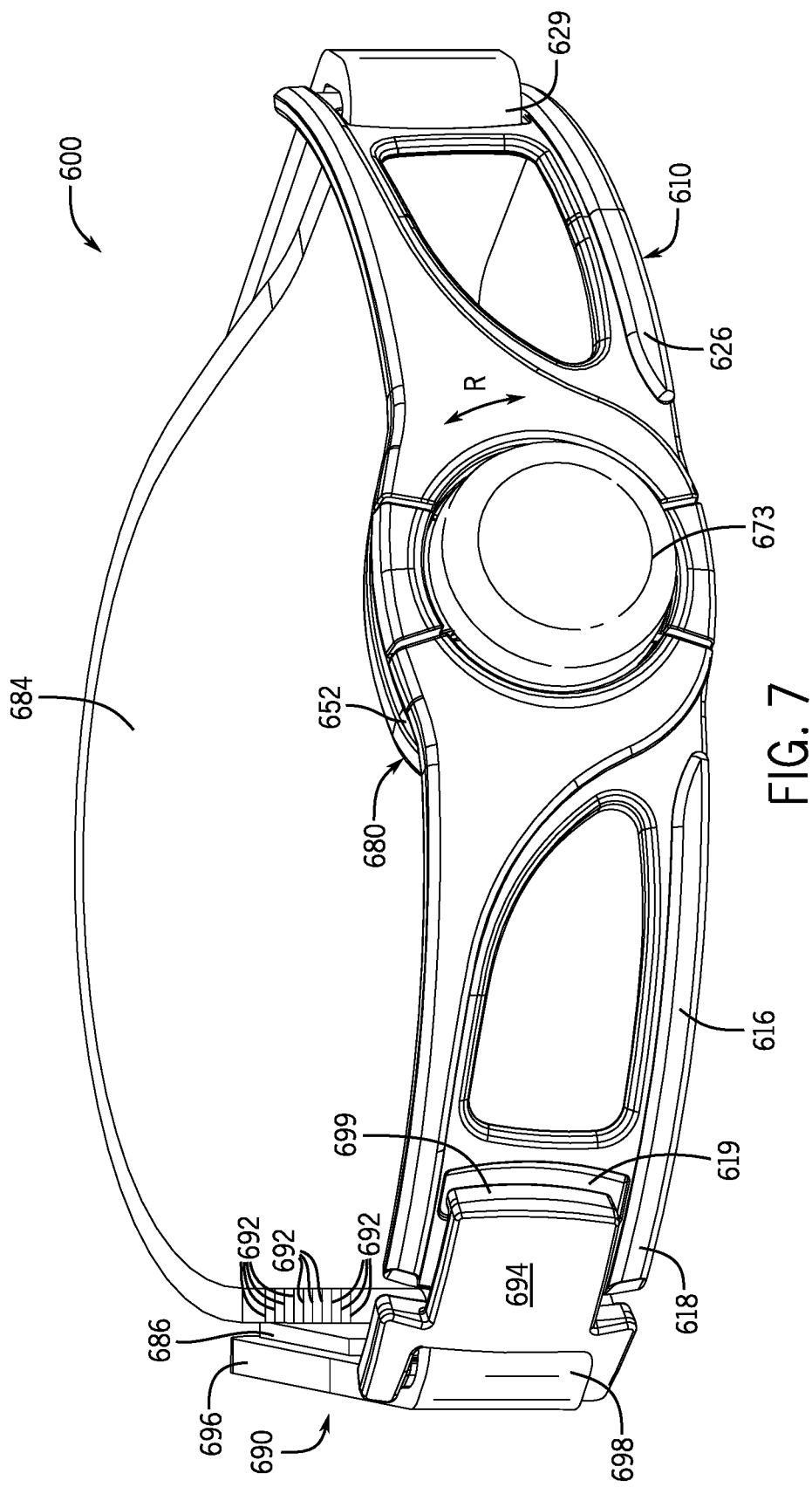
FIG. 7 is a right front perspective view of the device of FIG. 6.
Figure 8:
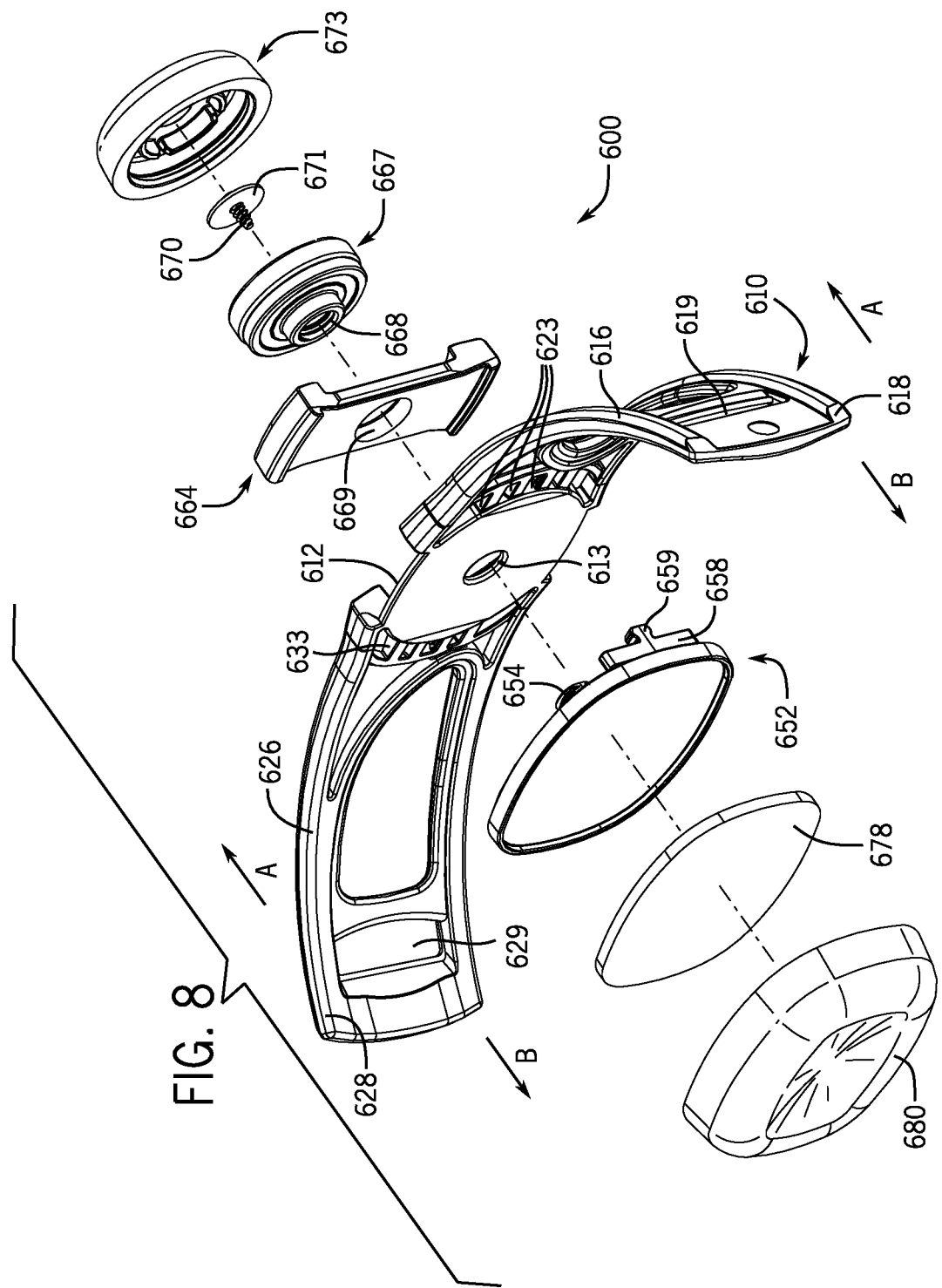
FIG. 8 is a top rear exploded perspective view of the device of FIG. 6 with the strap removed.
Figure 9:
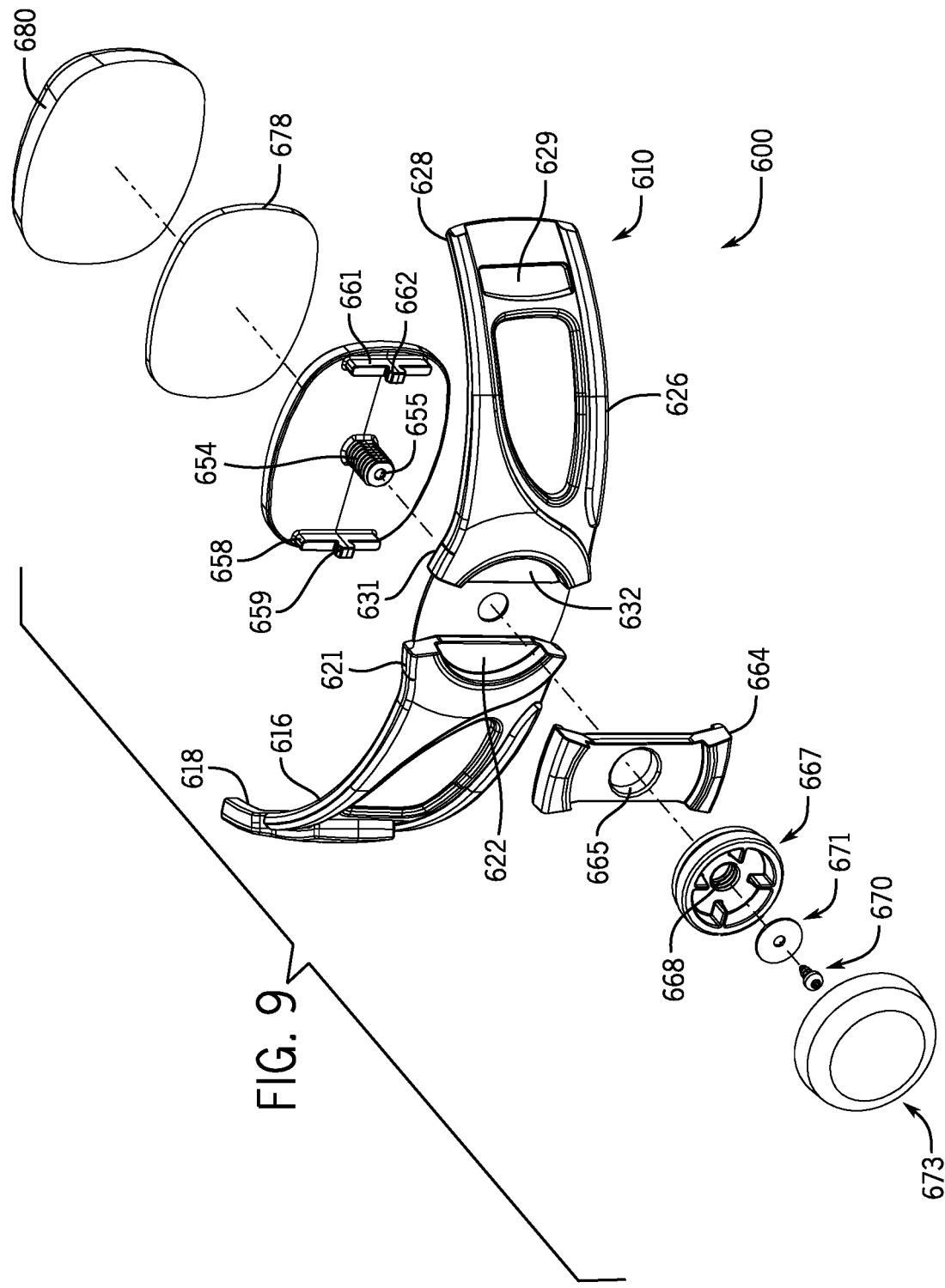
FIG. 9 is a top front exploded perspective view of the device of FIG. 6 with the strap removed.

Looking at FIGS. 6 and 7, the compression device 600 has a strap 684 including a first fastener 686 and a second fastener 688 that may each comprise the hook and loop fastening materials of a Velcro® fastener. A first reference line 690 and a plurality of additional reference lines 692 are also provided on the strap 684. The compression device 600 also has fastening clasp 694. A first end 696 of the strap 684 is inserted through a slot 698 of the clasp 694 and secured to the strap 684 by the first fastener 686. A second end 697 of the strap 684 is inserted through slot 629 of the frame 610 and secured to the strap 684 by the second fastener 688. An end 699 of the clasp 694 is fastened in the slot 619 of the frame 610.

The length of the cushion 680 along the long axis of the cushion 680 and a thickness of the cushion 680 is configured to apply minimal external pressure to the vascular structures within the neck, such as the carotid artery or the jugular veins. For example, the thickness of the cushion 680 allows for a gap of air between the compression device 600 and the neck in the proximity of the vascular structures. Here, the frame 610 and the strap 684 bridge over the carotid and jugular vein avoiding compression of these vital organs. The aforementioned bridge is between the cushion 680 and sternocleidomastoid muscle.

Turning now to FIGS. 10-13, any of the compression devices 200, 400, 600 can be used in conjunction with a pressure sensing device 700 to determine the external pressure that is to be used within the predetermined range for a specific patient. The pressure sensing device 700 has a housing 702 including a top section 704 and a bottom section 705 held together by screws 707. Inside the housing 702, a battery 709 is held in battery clips 711 that are in electrical communication with a printed circuit assembly 713. A digital display 715 is in electrical communication with the printed circuit assembly 713. A contact 717 is in electrical communication with the printed circuit assembly 713, and an on button 719 moves the contact 717 for turning on or off the digital display 715.

A pressure sensor 721 is in electrical communication with the printed circuit assembly 713, and the pressure sensor 721 has a tubular inlet 722. A conduit 724 places the inlet 722 of the pressure sensor 721 in fluid communication with a tubular outlet 727 of a male fitting 726 that is positioned between the top section 704 and the bottom section 705 of the housing 702. Looking at FIG. 12A, the pressure sensor 721 includes a case 772 having a cover 773. The pressure sensor 721 includes a sensing layer in the form of a silicon diaphragm 774. The sensing layer has a first side 791 and an opposite second side 792. The first side 791 of the diaphragm 774 contacts a gel die coat 778, and the second side 792 of the diaphragm 774 faces an opening 782 of the case 772. A sensing element 775 in the form of a strain gauge is connected to the diaphragm 774. An electrical lead 776 is in electrical communication with the sensing element 775 via a wire 777.

Figure 10:
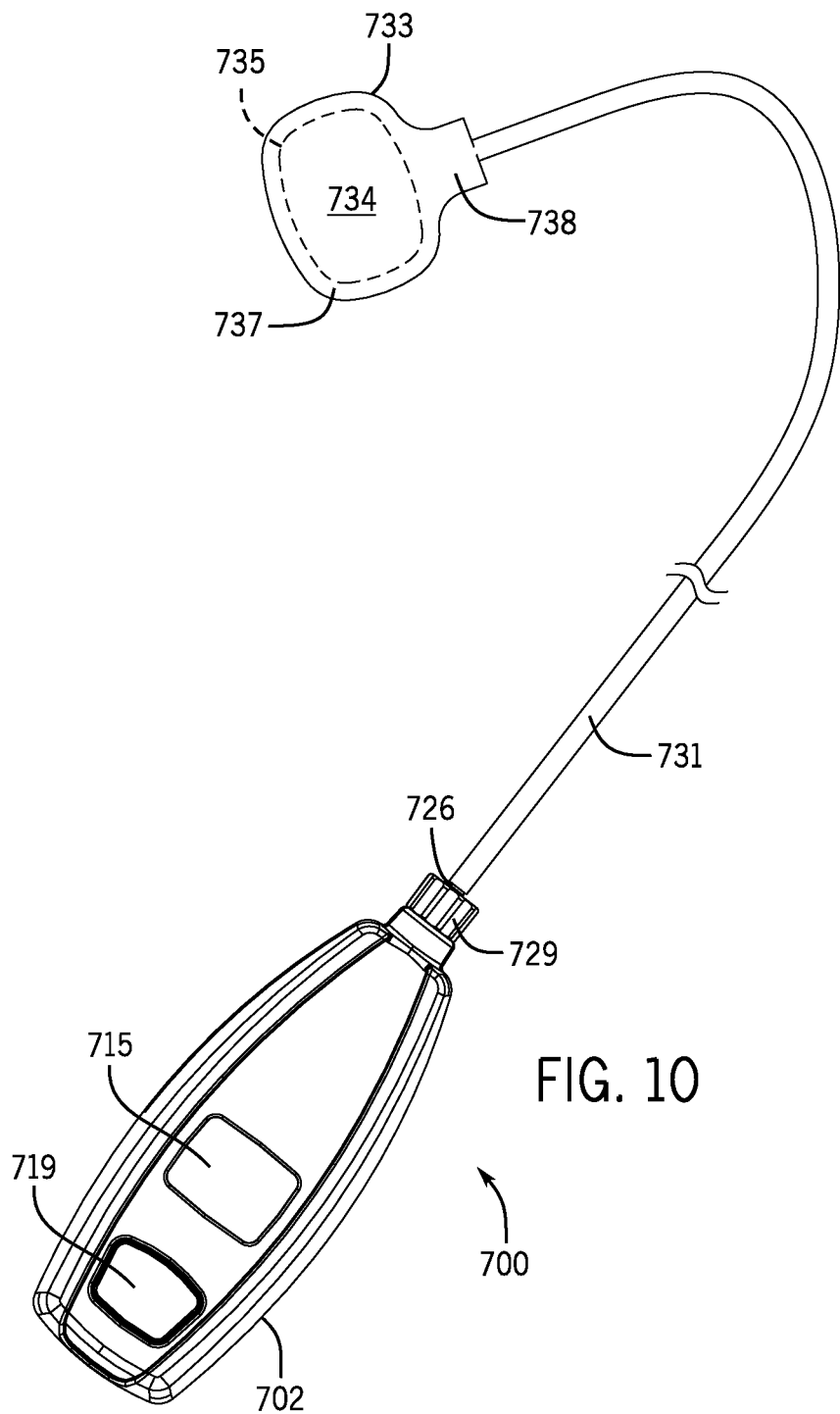
FIG. 10 is a top view of a pressure sensing device suitable for use with the device of FIG. 6.
Figure 11:
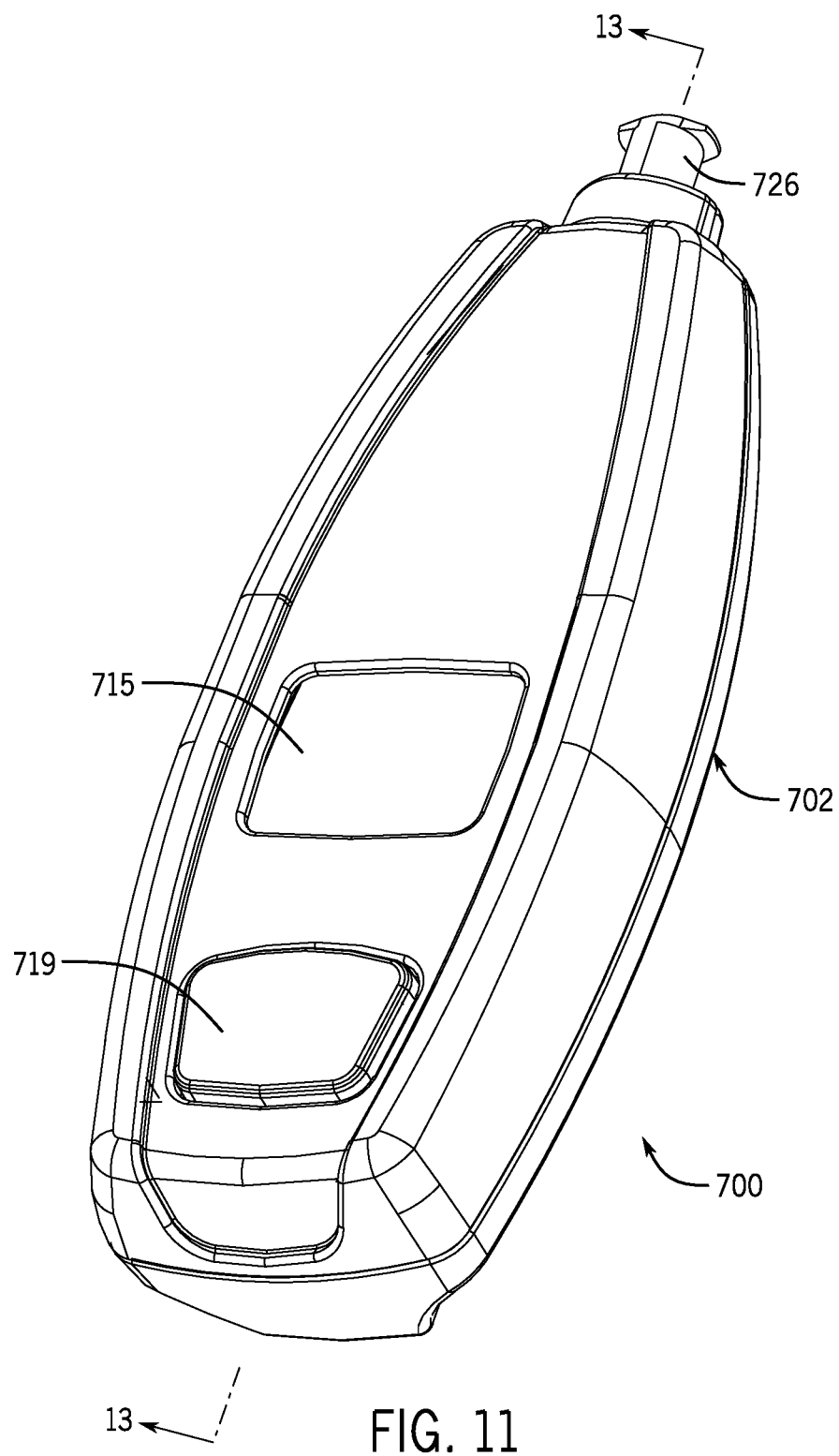
FIG. 11 is a right rear perspective view of the hand held unit of the pressure sensing device of FIG. 10 with the sensor tubing and attached sensor pouch removed.

A female fitting 729 connects to the male fitting 726 to place a length of tubing 731 in fluid communication with the pressure sensor 721. In one non-limiting example, the tubing 731 comprises transparent polyurethane, has a length of 12 inches, and has an inside diameter of 0.094 inches. A pouch 733 is secured with a fluid tight seal to a distal end of the tubing 731, and an open cell foam insert 735 is positioned in an interior space of the pouch 733. The interior space of the pouch 733 is in fluid communication with the tubing 731. In one non-limiting example, the pouch 733 is formed by RF heat sealing around a perimeter of two pieces of polyurethane film having a thickness of about 0.006 inches. The top piece 734 of polyurethane film is shown in FIG. 10, and the bottom piece (not shown) of polyurethane film has a perimeter substantially the same as the top piece 734. In the non-limiting example shown in FIG. 10, the pouch 733 has a main section 737, and has a connection section 738 that facilitates a fluid tight seal (e.g., a heat seal) with the tubing 731. In one non-limiting example, the main section 737 of the top piece 734 of the pouch 733 has a surface area of about 1 square inch. In one non-limiting example, the foam insert 735 comprises a 0.125 inch thick section of polyurethane open cell foam that has a perimeter shape similar to the perimeter shape of the main section 737 of the pouch 733. In one non-limiting example, the main section 737 of the pouch 733 has a volume of about 0.125 cubic inches.

Operation of the pressure sensing device 700 proceeds as follows. The tubing 731 with the female fitting 729 and attached pouch 733 are preferably provided as a disposable item in packaging. The female fitting 729 is connected to the male fitting 726. In one non-limiting example, the female fitting 729 and the male fitting 726 use a Luer taper connection. The connection creates a fluid (e.g., air) tight path between the pressure sensor 721 and the pouch 733. The connection is created at ambient atmospheric pressure such that the pressure within the tubing 731 and the pouch 733 is about atmospheric pressure.

The on button 719 is depressed to power up the printed circuit assembly 713 and turn on the digital display 715. A controller on the printed circuit assembly 713 can be programmed to provide continuous read out of pressure on the digital display 715 until the on button 719 is depressed a second time. Alternatively, the controller on the printed circuit assembly 713 can be programmed to provide continuous read out of pressure on the digital display 715 for a set time period before automatic power turn off. In one non-limiting example, automatic power turn off occurs two minutes after the on button 719 is depressed. The pouch 733 of the pressure sensing device 700 is then positioned between two surfaces, and as the surfaces move together to contact and apply pressure by compressing the pouch 733, the volume in the pouch 733 decreases thereby increasing pressure within the pouch 733 and attached tubing 731. The pressure sensor 721 senses the pressure increase, and the controller on the printed circuit assembly 713 executes a stored program to provide a read out of the applied pressure on the pouch 733 on the digital display 715 in mm Hg. The pressure sensor 721 may sense the pressure at fixed time intervals (e.g., 16 times a second).

Figure 12:
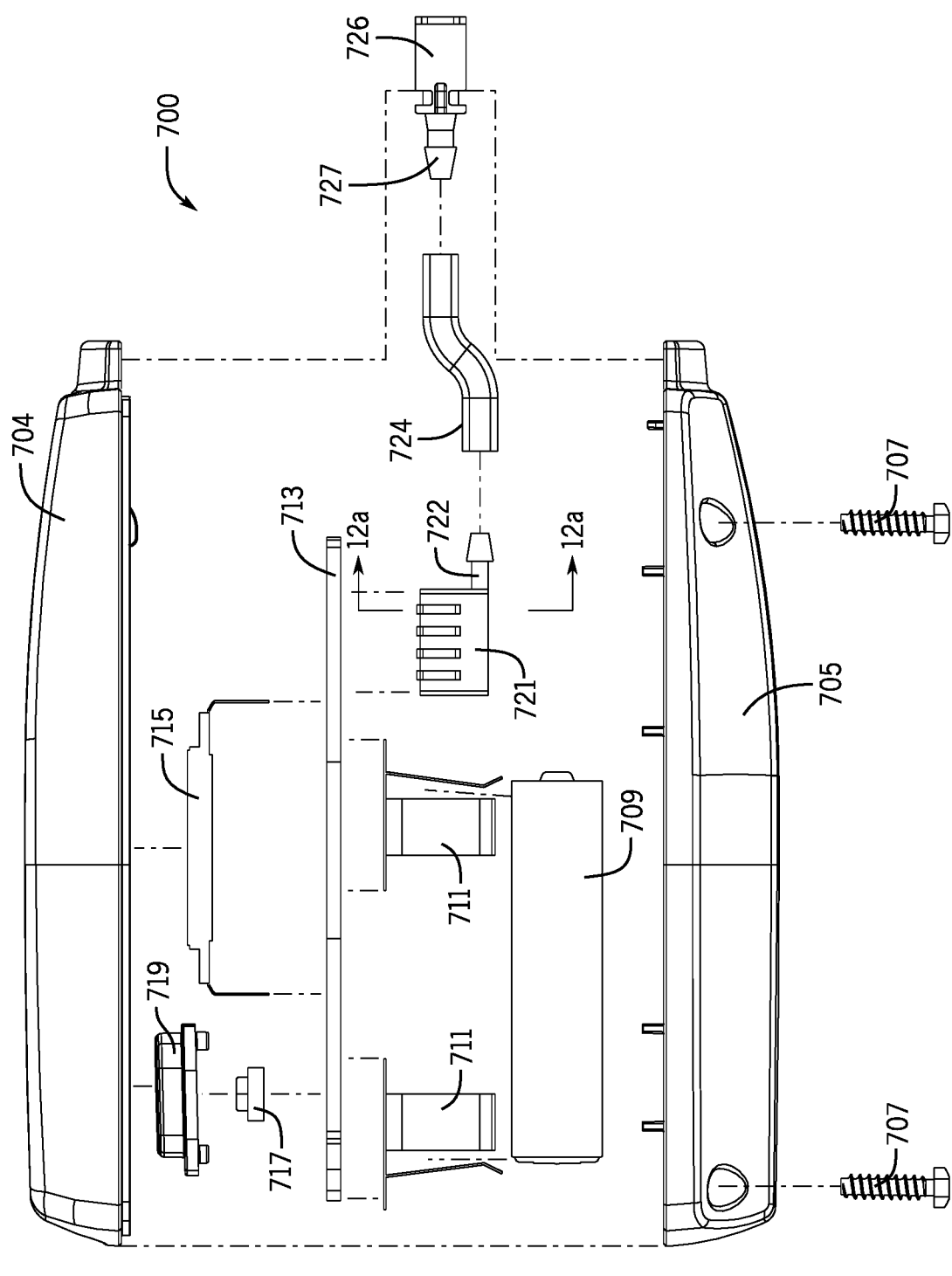
FIG. 12 is a side exploded view of the hand held unit of the pressure sensing device of FIG. 11.
Figure 12A:
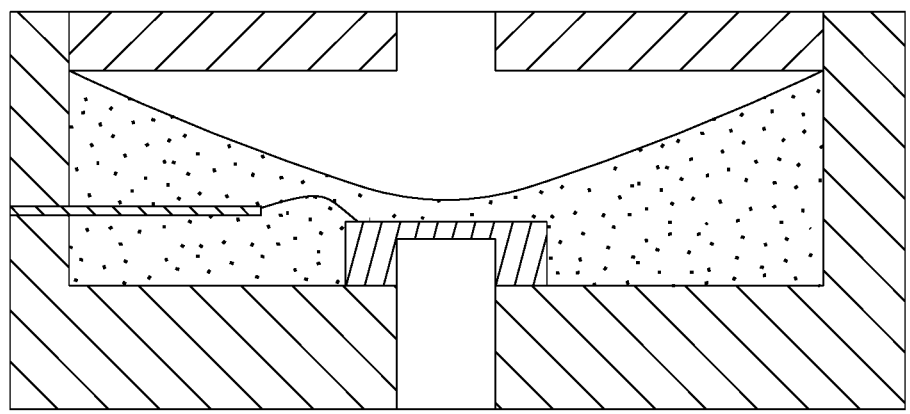
FIG. 12A is a cross-sectional view of the pressure sensor of the hand held unit of the pressure sensing device of FIG. 11 taken along line 12A-12A of FIG. 12.
Figure 13:
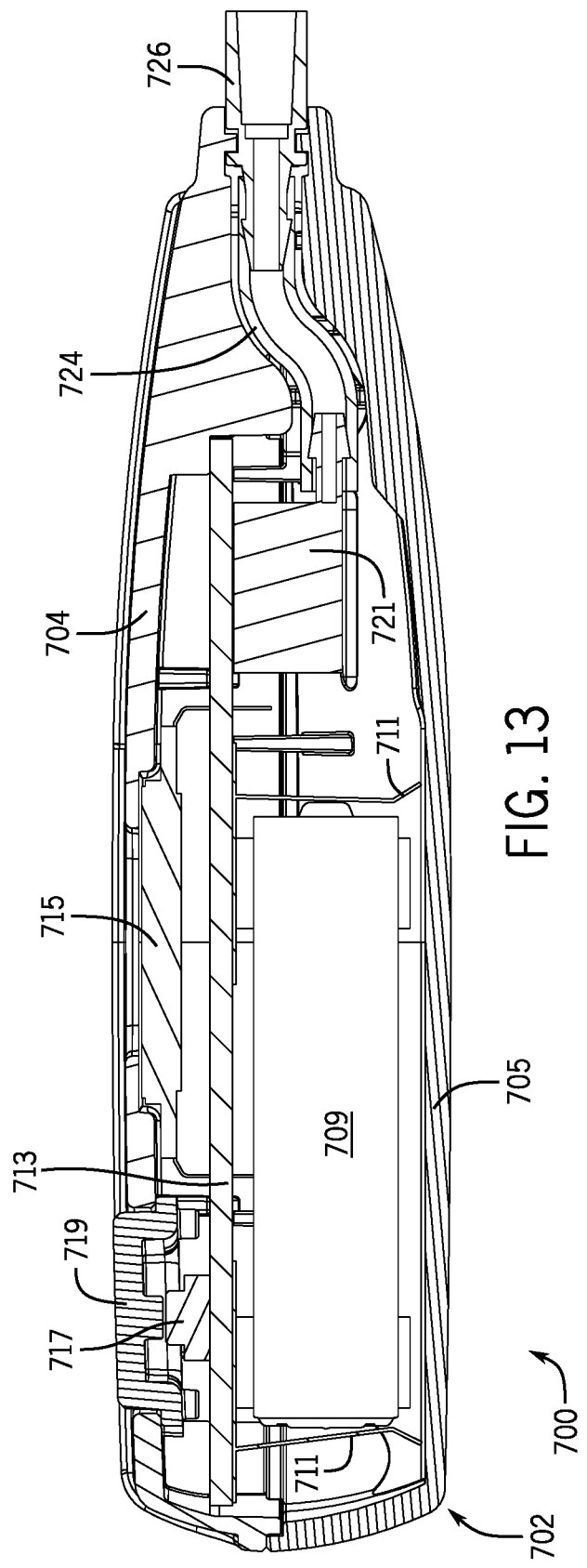
FIG. 13 is a cross-sectional view of the hand held unit of the pressure sensing device of FIG. 11 taken along line 13-13 of FIG. 11.

Looking at FIGS. 12 and 12A, the tubing 731 is in fluid communication with an opening 781 in the case 772 of the pressure sensor 721. The first side 791 of the diaphragm 774 senses a pressure of the fluid within the pouch 733 and attached tubing 731 via gel die coat 778. The second side 792 of the diaphragm 774 senses ambient atmospheric pressure via opening 782. A differential pressure measurement as an output voltage is obtained in which the pressure applied to the first side 791 of the diaphragm 774 is measured against the ambient atmospheric pressure. Specifically, applying pressure to the diaphragm 774 results in a resistance change in the strain gauge sensing element 775, which in turn causes a change in the output voltage in direct proportion to the applied pressure on the diaphragm 774.

Figure 14:
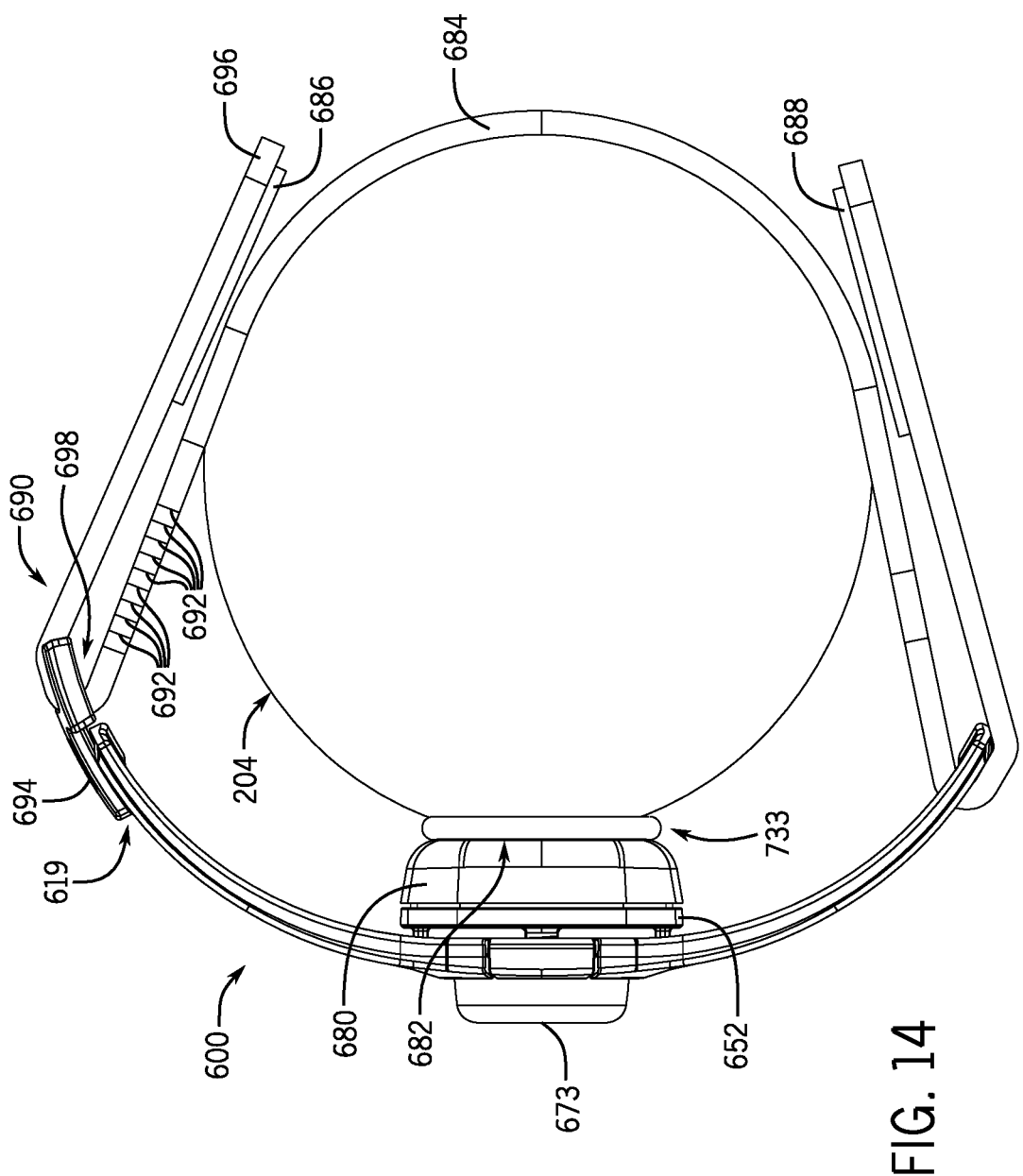
FIG. 14 is a schematic diagram depicting a transverse cross section of a patient's neck encircled by the compression device of FIG. 6.

Looking now at FIG. 14, the pouch 733 of the pressure sensing device 700 is shown positioned between a patient's neck 204 and the cushion 680 of the compression device 600 of FIGS. 6 to 9. The pouch 733 is put into contact with the anterior portion of the patient's neck 204 over the cricoid. The frame 610 of the compression device 600 is positioned such that the cushion 680 contacts the pouch 733. The strap 684 is placed around the neck 204, and the clasp on the strap 684 is fastened in the slot 619 of the frame 610 to secure the compression device 600 around the neck 204. In one non-limiting example, the main section 737 of the top piece 734 of the pouch 733 and the contact surface 682 of the cushion 680 have about the same surface area (e.g., about 1 square inch). The pressure exerted on the pouch 733 and cricoid is varied by unfastening the first end 696 from the strap 684, moving the strap 684 through the slot 698 of the clasp 694, and then refastening the first end 696 to the strap 684 by way of first fastener 686. The first reference line 690 and the plurality of additional reference lines 692 provide a visual indication of the tension on the strap 684. For example, when the first reference line 690 and a reference line 692 nearest the clasp 694 are aligned, a lower tension on the strap 684 and a lower pressure on the pouch 733 and cricoid are exhibited compared to when the first reference line 690 and a reference line 692 furthest from the clasp 694 are aligned.

Figure 15:
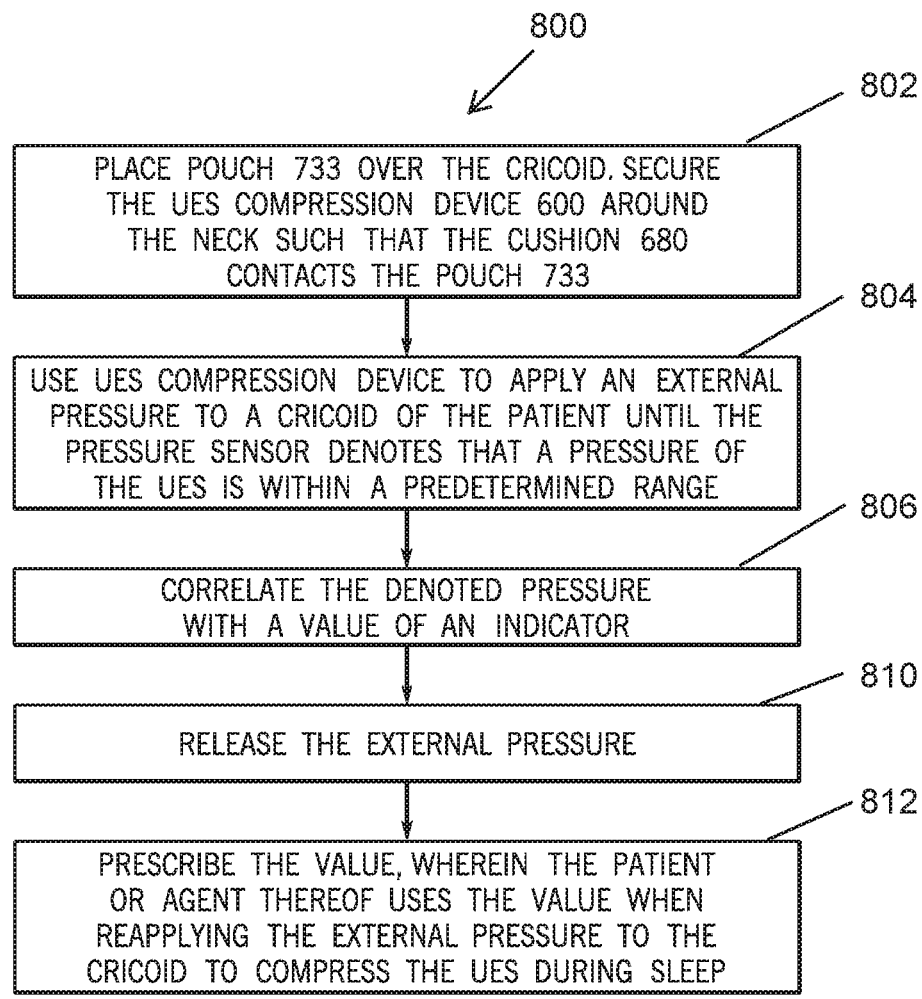
FIG. 15 is a summary of a method for compressing the UES of a patient to reduce gastroesophageal and gastroesophagopharyngeal reflux.

Referring now to FIG. 15, a flow diagram summarizes a method 800 for compressing the upper esophageal sphincter of a patient to reduce gastroesophageal and gastroesophagopharyngeal reflux during sleep. At step 802, the pouch 733 of the pressure sensing device 700 is attached to the anterior portion of the patient's neck 204 over the cricoid. A cushion 680 (which may be removed from packaging) is secured to the adjustment plate 652 of the frame 610 of the compression device 600. The frame 610 of the compression device 600 is then positioned such that the cushion 680 contacts the pouch 733. The strap 684 is placed around the neck 204, and the clasp 694 on the strap 684 is fastened in the slot 619 of the frame 610 to secure the compression device 600 around the neck 204.

At a step 804, the compression device 600 is used to apply an external pressure to the cricoid of the patient. The external pressure is varied by unfastening and refastening the first end 696 and/or the second end 697 to the strap 684 at different positions until the digital display 715 of the pressure sensing device 700 denotes that the pressure of the UES is within a predetermined range, such as between about 10-70 mm Hg, preferably 20-30 mm Hg. This predetermined range is ideally in a range that allows the upper esophageal sphincter to open to vent gas or allows belching, or allows swallowing or high pressure vomiting. Studies have confirmed that the pressure displayed on the digital display 715 of the pressure sensing device 700 has about a 1:1 relationship to the intra-luminal pressure for a specific patient. This 1:1 relationship can be achieved with suitable programming of the controller, e.g., the printed circuit assembly 713.

At a step 806, the value of an indicator can be associated with the applied external pressure. For example, the alignment of the first reference line 690 and one of the plurality of additional reference lines 692 on both sides of the strap 684 can be the indicator.

At the step 810, the compression device 600 is removed from the patient's neck such that the external pressure is removed. At the step 812, the value for the indicators is prescribed. In this manner, an intra-luminal pressure sensor is not required to determine if the appropriate external pressure is being applied to induce the intra-luminal pressure that is within the predetermined range.

The clasp 694 allows the patient to unfasten the strap 684 from the frame 610 and then refasten the strap 684 to compress the upper esophageal sphincter at the prescribed pressure for a duration of time, such as during sleep for example. The patient, or agent thereof, can use the value of the indicator to reattach the strap 684 to the frame 610 and the clasp 694 in the prescribed position after removal of the strap 684 from the frame 610 (such as for washing).

A practitioner (e.g., a nurse or doctor) may use the steps of FIG. 15 and a kit (e.g., a compression device 600 and a pressure sensing device 700) to determine a prescription to reduce gastroesophageal and gastroesophagopharyngeal reflux in a patient during sleep. The practitioner notes which of the plurality of additional reference lines 692 of the strap 684 of the compression device 600 aligns with the first reference line 690 on each side of the strap 684 when the strap 684 is positioned to produce the desired intra-luminal pressure (step 806). The practitioner prescribes that the UES compression device 600 is to be intermittently worn at the selected alignment of the reference lines by the patient for a duration, such as during sleep (step 812). The prescription may be for the patient to use the UES compression device for a period of time, such as several days (nights), weeks, months, years, or a lifetime.

In some implementations, the patient may return to repeat the steps 802 through 812. Therefore, from time to time, the prescription may need adjusting and/or a new prescription may need to be given. However, the adjustment mechanism for the frame 610 as described above can allow a patient to easily make smaller scale adjustments in the pressure such as for comfort. When a patient wearing the compression device 600 rotates the adjustment knob 673 in one direction R of FIG. 7 (e.g., clockwise), the first section 616 of the frame 610 moves in direction A of FIG. 8 with respect to the central section 612 of the frame 610, and the second section 626 of the frame 610 moves in direction A of FIG. 8 with respect to the central section 612 of the frame 610. This results in an increase in pressure on the cricoid. When a patient wearing the compression device 600 rotates the adjustment knob 673 in the opposite direction R of FIG. 7 (e.g., counterclockwise), the first section 616 of the frame 610 moves in direction B of FIG. 8 with respect to the central section 612 of the frame 610, and the second section 626 of the frame 610 moves in direction B of FIG. 8 with respect to the central section 612 of the frame 610. This results in a decrease in pressure on the cricoid. Thus, without intending to limit the scope of the invention, the prescription steps of FIG. 15 could be described as "macro pressure adjustment", and the use of the adjustment knob 673 of the adjustment mechanism of the frame 610 of the compression device 600 could be described as "micro pressure adjustment". The "macro pressure adjustment" provided by the strap 684 can also be done by the patient. The number of turns of the adjustment knob 673 can be correlated to some adjustments in pressure. For example, two full turns of the adjustment knob 673 may cause two millimeters of movement of the frame 610 and a corresponding change in pressure.

Figure 16:
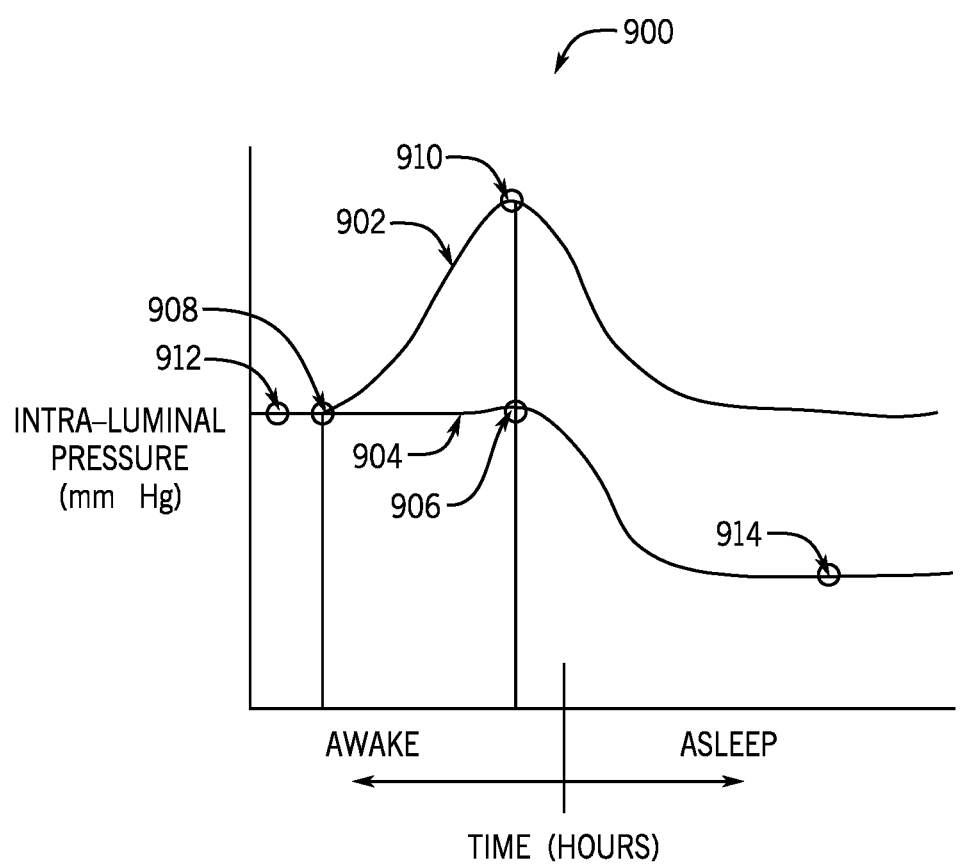
FIG. 16 is a graph depicting variations in intra-luminal pressure during awake and sleep stages of a patient suffering from gastroesophageal and gastroesophagopharyngeal reflux.

Referring to FIG. 16, a graph depicts variations in pressure; the UES during awake and sleep stages of a patient suffering from gastroesophageal and gastroesophagopharyngeal reflux. The Y-axis depicts the intra-luminal pressure in mm Hg and the X-axis depicts time measured in hours. The two graph lines show the intra-luminal pressure of the patient using a UES compression device (graph line 902) and not using a UES compression device (graph line 904). The resting level of the intra-luminal pressure for the patient is denoted at pressure 912, which is typically about 40 mm Hg. For the patient using the UES compression device, the compression device begins applying pressure to the cricoid of the patient at time 908 shown on graph line 902. The intra-luminal pressure is increased until the value of the indicator is at a prescribed level 910. At time 906, the patient begins to fall asleep. For the patient using the UES compression device, as the patient falls asleep the intra-luminal pressure decreases to the predetermined level that is induced by the compression device. In contrast, for the patient not using the UES compression device, the intra-luminal pressure decreases to approximately 10 mm Hg or below and remains at approximately 10 mm Hg or below (graph line 904 at pressure level 914) throughout the sleeping stage, leaving the patient susceptible to another episode of gastroesophageal and gastroesophagopharyngeal reflux. Graph line 902 in FIG. 16 shows the rise in intra-luminal pressure to be about equal to the fall in intra-luminal pressure as the patient using the compression device falls asleep. However, the rise and fall may have different values (e.g., 30 mm Hg rise as the patient tightens the compression device and 20 mm Hg fall as the patient falls asleep or visa versa). In certain implementations, the UES compression device is used to increase the intra-luminal pressure while the patient is asleep, raising the intra-luminal pressure from approximately 10 mm Hg to approximately 40 mm Hg, for example. In certain implementations, the UES compression device is reusable. In other implementations, the UES compression device is disposable.

The invention is not limited to the management or treatment of abnormal upper esophageal sphincter functionality. For example, the compression device 600 can provide a means for strengthening an esophageal sphincter of a subject. The term "subject" means an animal such as a mammal, preferably a human. A subject's lower or upper esophageal sphincter may be weakened due to disease or aging. This may make it difficult for the esophageal sphincter to stay closed. A leaky lower and/or upper esophageal sphincter may result. The compression device 600 can be used in a method for strengthening an esophageal sphincter of a subject. In the method, the compression device 600 is positioned around a neck of the subject such that the cushion 680 applies pressure on the neck that is transmitted to an esophageal sphincter of the subject. The step of positioning the compression device 600 can be repeated a number of times, for example, each night when the subject sleeps. The compression device 600 acts on the esophageal sphincter in a manner analogous to isometric exercise whereby the esophageal sphincter of the subject is strengthened. A subject with a strengthened upper esophageal sphincter may no longer require use of the compression device.

The compression device 600 can be used in conjunction with electrical stimulation to strengthen the esophageal sphincter of the subject. For example, one or more electrodes can be placed in contact with a cricoid region of the neck of the subject. The electrode(s) can be separate from the compression device 600, or the electrode(s) can be attached to a part of the compression device 600 such as the cushion 680. An electrical pulse generator is placed in electrical communication with each electrode. The electrical pulse generator is activated to generate a series of electrical pulses from each electrode, wherein the series of electrical pulses electrically stimulate the esophageal sphincter of the subject, thereby strengthening the esophageal sphincter. Thus, the compression device 600 can be part of a system that can be used to create electric impulses targeted at the UES at periodic intervals so as to improve muscle function of the UES. In another version of using electrical stimulation to strengthen the esophageal sphincter of the subject, the one or more electrodes is implanted on a surface of the esophagus adjacent the esophageal sphincter. In yet another version of using electrical stimulation to strengthen the esophageal sphincter of the subject, the one or more electrodes is placed in the upper esophageal sphincter of the subject.

The compression device 600 also provides a means for curing esophageal reflux disease of a subject. In the method, the compression device 600 is positioned around a neck of the subject such that the cushion 680 applies pressure on the neck that is transmitted to an esophageal sphincter of the subject. The step of positioning the compression device 600 can be repeated a number of times, for example, each night when the subject sleeps. The compression device 600 acts on the esophageal sphincter in a manner analogous to isometric exercise whereby the esophageal sphincter of the subject is strengthened. Without intending to be bound by theory, it is hypothesized that as a result of this strengthening of the esophageal sphincter, esophageal reflux disease of the subject can be cured.

The compression device 600 also provides a means for improving vocal function in a subject. It is estimated that laryngectomies number between 50,000 and 100,000. A speech pathologist works with those having a laryngectomy to recover or improve vocal function. The speech pathologist can work to find a pressure spot over a voice box region on the neck where vocal function in a subject is improved. The compression device 600 is then positioned over the voice box region of the neck of the subject such that the cushion 680 applies pressure to the spot over the voice box region of the neck of the subject. Vocal function of the subject is thereby improved.

The compression device 600 may also be used in the following applications: (1) assistance during mechanical ventilation to manage lung aspiration due to involuntary lack of cognitive control of the UES; (2) positioning or stabilizing of neck internal anatomical structures through the use of a mechanical assist device for injury or trauma recovery; (3) positioning or stabilizing of neck internal anatomical structures through the use of a mechanical assist device for surgical recovery; (4) assistance to apply cricoid pressure during anesthesia intubation using the Sellick maneuver and for rapid sequence induction; (5) positioning or stabilizing to immobilize subject neck during radiation treatment sessions and to avoid radiation overexposure to surrounding tissue leading to more targeted tumor treatment; and (6) positioning or stabilizing to apply consistent pressure that manipulates internal anatomical structures into optimal image position during ultrasound or other CT or MRI imaging wherein this may apply to other anatomical structures other than neck where the assist device can be positioned around, for example, the neck, head, shoulder, arm, or leg extremities.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method for strengthening an esophageal sphincter of a subject, the method comprising:
    (a) providing a compression device including (i) a frame, (ii) a strap having a first end section attached to the frame and an opposite second end section attached to the frame, and (iii) a cushion disposed on the frame;
    (b) positioning the compression device around a neck of the subject such that the cushion applies pressure on the neck that is transmitted to the esophageal sphincter of the subject; and
    (c) repeating step (b) a plurality of times whereby the esophageal sphincter of the subject is strengthened.

2. The method of claim 1 wherein:
    step (b) occurs while the subject is sleeping.

3. The method of claim 1 wherein:
    a length of the strap between the first end section and the second end section is adjustable,
    a clasp is attached to the second end section of the strap; and
    the clasp is configured to fasten the strap to the frame to position the cushion over a cricoid of the subject and to apply the pressure on the neck that is transmitted to the esophageal sphincter of the subject.

4. The method of claim 1 wherein:
    the clasp is configured to unfasten the strap from the frame and to refasten the strap to the frame to reapply the pressure on the neck that is transmitted to the esophageal sphincter of the subject.

5. The method of claim 1 wherein:
    the second end section of the strap is looped through a slot of the clasp for securing the second end section of the strap to the frame.

6. The method of claim 1 wherein:
    the compression device further comprises an adjustment mechanism for moving the cushion toward or away from the frame.

7. The method of claim 6 wherein:
    the adjustment mechanism is configured to perform micro-pressure adjustments to the pressure on the neck.

8. The method of claim 1 wherein:
    step (b) further comprises placing an electrode in contact with the neck of the subject, placing an electrical pulse generator in electrical communication with the electrode, activating the electrical pulse generator to generate a series of electrical pulses from the electrode such that the series of electrical pulses electrically stimulate the esophageal sphincter of the subject, and the electrode is attached to the cushion.

9. The method of claim 1 wherein:
    step (b) further comprises placing an electrode adjacent or in the esophageal sphincter, placing an electrical pulse generator in electrical communication with the electrode, activating the electrical pulse generator to generate a series of electrical pulses from the electrode such that the series of electrical pulses electrically stimulate the esophageal sphincter of the subject.

10. The method of claim 1 wherein:
the pressure on the neck that is transmitted to the esophageal sphincter of the subject induces an intra-luminal upper esophageal sphincter pressure to remain within a range that is 10-70 mm Hg.

11. A method for improving esophageal reflux disease of a subject, the method comprising:
   (a) providing a compression device including (i) a frame, (ii) a strap having a first end section attached to the frame and an opposite second end section attached to the frame, and (iii) a cushion disposed on the frame; and
   (b) positioning the compression device around a neck of the subject such that the cushion applies pressure to a cricoid of the subject; and
   (c) repeating step (b) a plurality of times whereby the esophageal reflux disease of the subject is improved.

12. The method of claim 11 wherein:
step (b) occurs while the subject is sleeping.

13. The method of claim 11 wherein:
a length of the strap between the first end section and the second end section is adjustable,
a clasp is attached to the second end section of the strap; and
the clasp is configured to fasten the strap to the frame to position the cushion over a cricoid of the subject and to apply the pressure on the neck that is transmitted to the esophageal sphincter of the subject.

14. The method of claim 11 wherein:
the clasp is configured to unfasten the strap from the frame and to refasten the strap to the frame to reapply the pressure on the neck that is transmitted to the esophageal sphincter of the subject.

15. The method of claim 11 wherein:
the second end section of the strap is looped through a slot of the clasp for securing the second end section of the strap to the frame.

16. The method of claim 11 wherein:
the compression device further comprises an adjustment mechanism for moving the cushion toward or away from the frame, and
the adjustment mechanism is configured to perform micro-pressure adjustments to the pressure on the neck.

17. The method of claim 11 wherein:
the pressure applied to the cricoid of the subject induces an intra-luminal upper esophageal sphincter pressure to remain within a range that is 10-70 mm Hg.

\* \* \* \* \*

UNITED STATES PATENT AND TRADEMARK OFFICE
CERTIFICATE OF CORRECTION

PATENT NO. : 10,709,456 B2  
APPLICATION NO. : 15/997153  
DATED : July 14, 2020  
INVENTOR(S) : Nick T. Maris et al.

Page 1 of 1

It is certified that error appears in the above-identified patent and that said Letters Patent is hereby corrected as shown below:

In the Specification

Column 1, Line 1. Please insert:
--This invention was made with government support under RR031973 and TR000055 awarded by the National Institutes of Health. The government has certain rights in the invention.--

Signed and Sealed this
Sixth Day of October, 2020

Andrei Iancu
*Director of the United States Patent and Trademark Office*